United States Patent [19]
Brudnoy et al.

[11] Patent Number: 6,115,674
[45] Date of Patent: Sep. 5, 2000

[54] AUTOMATED DETECTION AND LOCATION OF INDICATIONS IN EDDY CURRENT SIGNALS

[75] Inventors: David M. Brudnoy, Albany; Jane E. Oppenlander, Burnt Hills; Arthur J. Levy, Schenectady, all of N.Y.

[73] Assignee: The United States of America as represented by the United States Department of Energy, Washington, D.C.

[21] Appl. No.: 09/107,142

[22] Filed: Jun. 30, 1998

[51] Int. Cl.$^7$ .................................................. G06F 19/00

[52] U.S. Cl. ........................... 702/38; 702/190; 702/191; 324/238

[58] Field of Search .................... 72/35, 36, 38, 72/190, 191; 324/232, 238

[56] References Cited

U.S. PATENT DOCUMENTS

| | | | |
|---|---|---|---|
| 5,339,256 | 8/1994 | Levy et al. | 702/38 |
| 5,424,640 | 6/1995 | Levy | 324/238 |
| 5,737,445 | 4/1998 | Oppenlander et al. | 702/191 |
| 5,825,672 | 10/1998 | Brudnoy | 702/190 |

*Primary Examiner*—Marc S. Hoff
*Assistant Examiner*—Bryan Bui
*Attorney, Agent, or Firm*—John T. Lucas; William R. Moser; Paul A. Gottlieb

[57] ABSTRACT

A computer implemented information extraction process that locates and identifies eddy current signal features in digital point-ordered signals, signals representing data from inspection of test materials, by enhancing the signal features relative to signal noise, detecting features of the signals, verifying the location of the signal features that can be known in advance, and outputting information about the identity and location of all detected signal features.

11 Claims, 24 Drawing Sheets

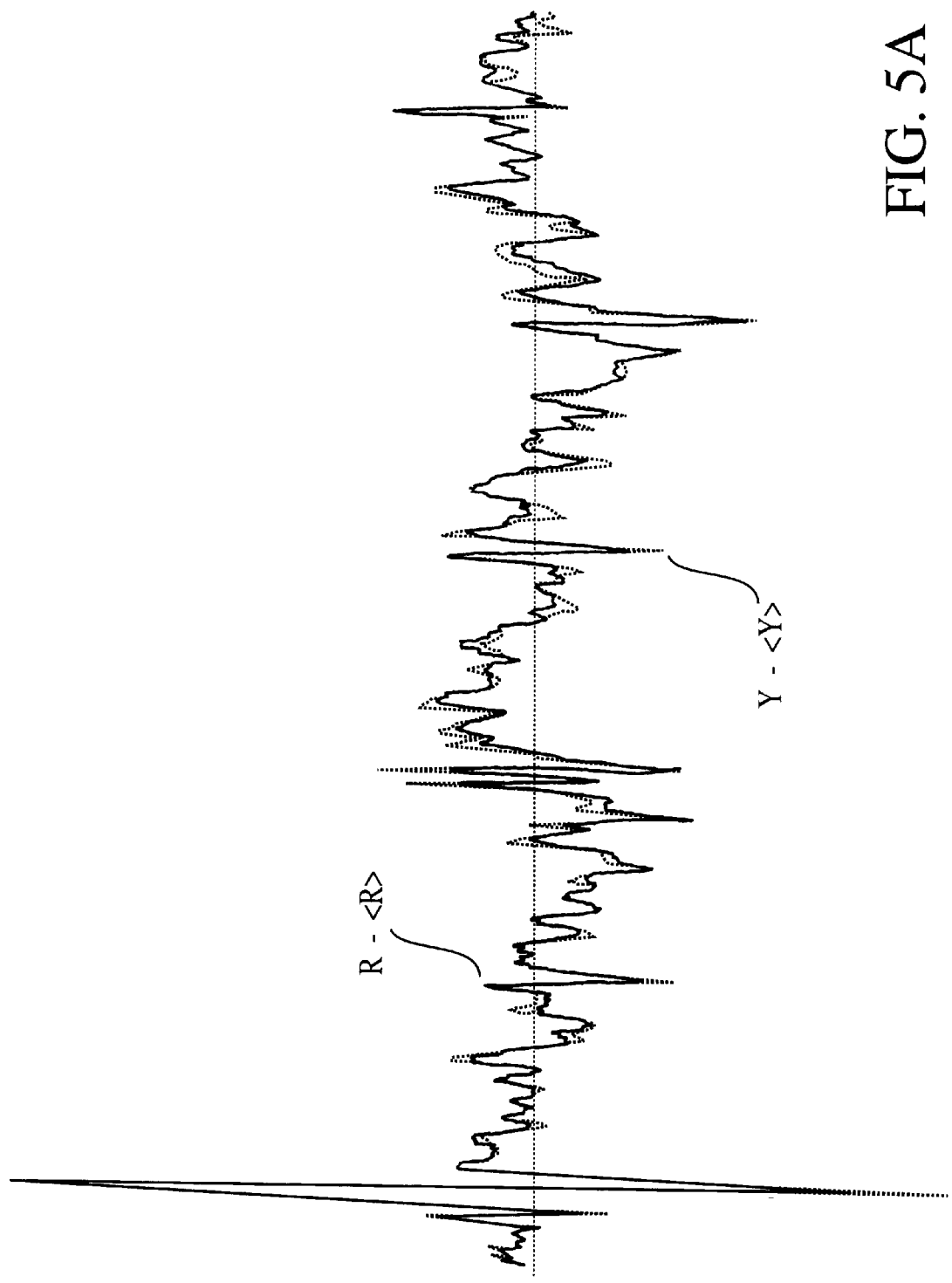

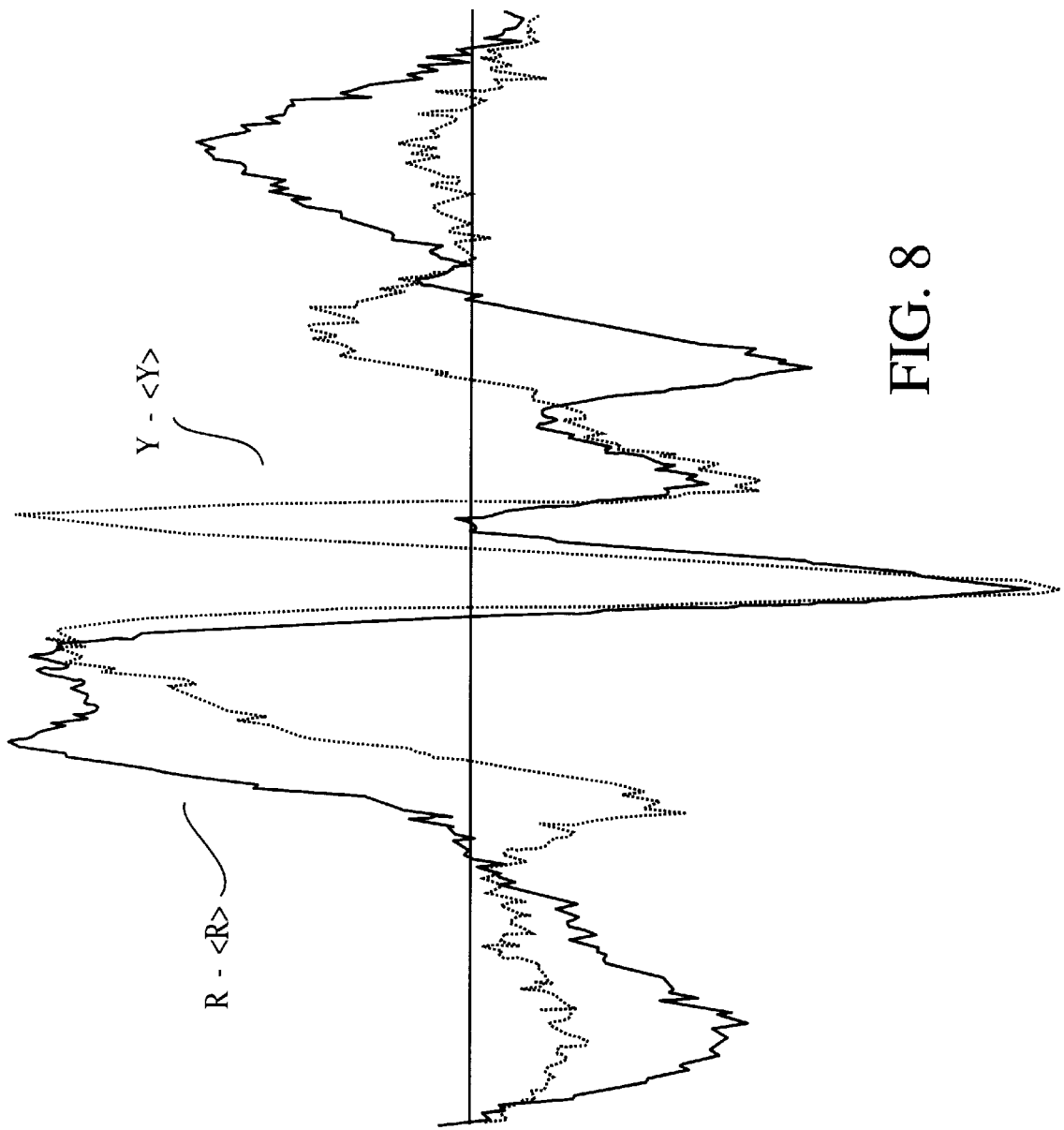

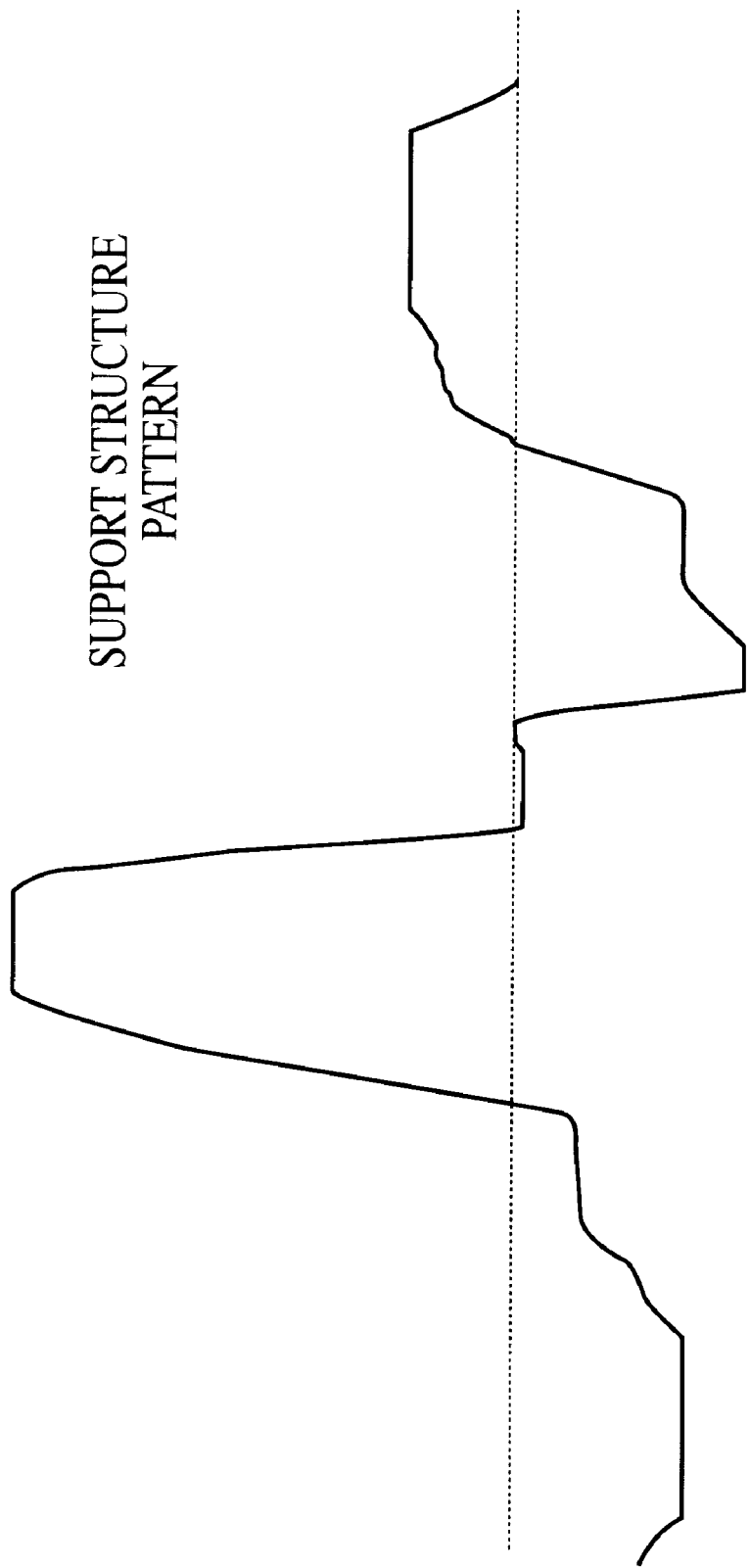

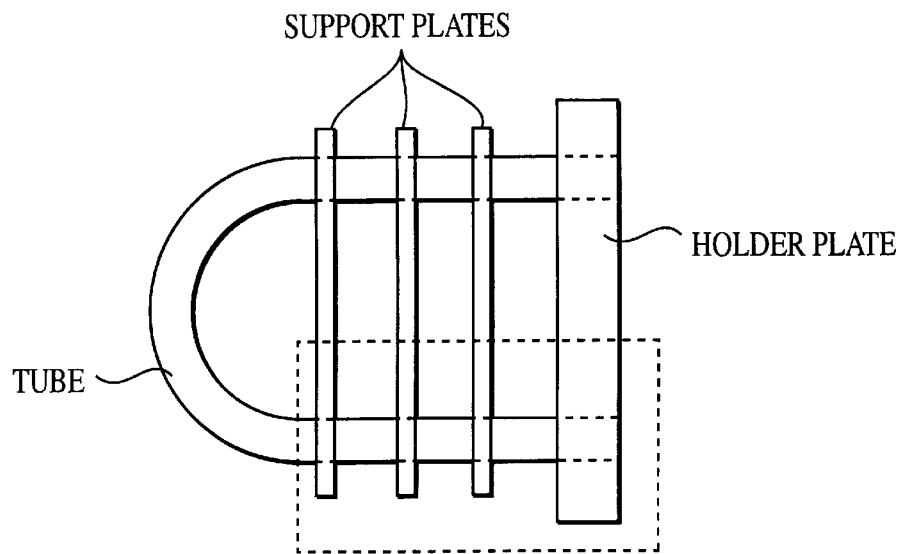
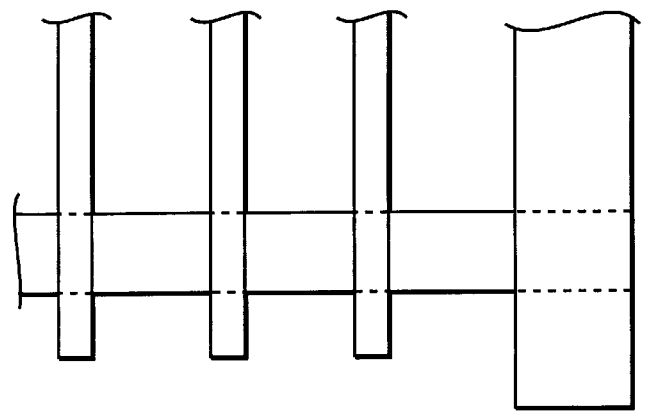
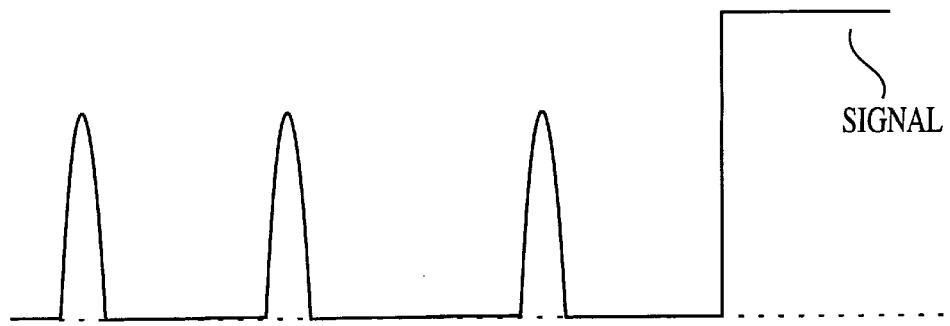
FIG. 12

AUTOMATED DETECTION AND LOCATION OF INDICATIONS IN EDDY CURRENT SIGNALS

This is a finalized application of Provisional Ser. No. 60/051,208 filed Jun. 30, 1997.

FIELD OF INVENTION

The present invention relates to the field of non-destructive testing of material parts. More particularly it relates to computer-implemented automated detection and location of indications in eddy current signals.

BACKGROUND OF THE INVENTION

Eddy current testing (ET) is a non-destructive method for inspecting metallic parts. It involves the use of an electromagnetic probe with one or more coils that move across the surface of a test piece, inducing electrical currents (eddy currents) in the test piece near the probe. Since discontinuities in a metal such as a flaw can alter the flow of eddy currents, thereby changing the electromagnetic impedance of the coil, measurement of probe impedance can provide the information needed to locate and identify discontinuities in the material.

The processing of ET signals is often performed by human analysts, who visually inspect signals in search of patterns that indicate the presence of a material defect. In some cases, an indication is visually prominent, thus easily identified, while, in other cases, an indication pattern is either similar to or obscured by signal background patterns, thus difficult to locate. Since signal inspection is a visual skill based on subjective judgement, it is not unusual to find that different analysts inspecting the same signal sometimes come to different conclusions; even the same analyst may produce different conclusions for the same data inspected at different times.

Prior attempts have been made to automate eddy current inspection procedures. In particular, such attempts are disclosed in U.S. Pat. No. 4,628,261, issued to Huschelrath et al.; U.S. Pat. No. 4,821,204, issued to Huschelrath et al.; U.S. Pat. No. 4,979,124, issued to Sachse et al. and U.S. Pat. No. 5,144,565, issued to Brown et al.

A common feature of these methods is their analytic approach, as opposed to the utilization of visual methods. Another common feature of these prior methods is the requirement of pre-test learning from similar physical systems. Consequently, significant amounts of input information in these methods must be derived from external test systems. Prior methods assume that there is a set of measurable geometric and/or electrical parameters whose values suffice to uniquely locate and interpret an indication. The present method makes no such assumption, does not attempt to interpret indications, and claims only detection capability.

It is an object of the present invention to provide automated eddy current scanning, thereby rendering ET signal analysis more objective and repeatable. The invention is based on general methods that emulate two important characteristics of human visual skills: global perception and reasoning with shapes. Global perception means that an entire signal, rather than individual data points, is treated as the fundamental object of processing. Reasoning with shapes means that signals are analyzed by considering their geometric form rather than their quantitative behavior. This approach is appropriate for automated ET scanning because it emulates the methods used by ET analysts: applying visual skills to identify visual patterns.

It is a further object of the present invention to provide processing of ET signals in which human visual characteristics are emulated through the use of two image processing methods, mathematical morphology and pattern recognition. Under such processing, information is extracted, and indications identified, by performing appropriate sequences of morphological processing using geometric filters. Sequential filtering is the practical implementation of the concept of global perception using visual shape-reasoning.

SUMMARY OF THE INVENTION

The process of the present invention emulates the human visual system by treating the signal, or major signal segments, in their entirety, and operating on signals with geometric filters. The methods are capable of providing: (1) automatic and autonomous identification of ET signal patterns indicating the presence of material discontinuities, such as flaws, in a test piece; (2) automatic and autonomous identification of ET signal patterns indicating the presence of known external features along a test piece; these locations serve as reference points correlating signal to test piece positions; (3) verification, or rejection, of the locations of the external features by comparison with design specifications; (4) automatic and autonomous quantitative determination of local noise levels of an ET signal.

The term "automatic" refers to methods capable of computer-implementation, while "autonomous" refers to the capability of applying the invention using only internal test system information. Examples of test system information include, but are not restricted to, test piece dimensions and configurations, measurement rates, resolution limits of the measurement instruments, and specified criteria for acceptance of results. Other relevant information is derived whenever necessary, based on the emulation of visual "observations" of a human analyst. For example, in addition to (a priori unknown) anomaly indications, ET signals may contain known patterns produced by known test piece structural members. Because a test piece may be only partially scanned, however, the number of structural patterns in a signal cannot be known in advance of visual inspection. By emulating visual observation, the methods of this invention will determine what part of the test piece was actually scanned. The extent of autonomy manifested by this invention, i.e., its ability to detect and locate indications with merely a paucity of input information, is a novel feature of this invention.

BRIEF DESCRIPTION OF THE DRAWINGS

In order to emphasize the visual aspect of this invention, all signals displayed in the accompanying figures do not include axes; in this manner, attention is focused on geometric shape rather than physical units or quantitative values.

FIG. 8 depicts: an ET signal with indication in support structure region, impedance components, R (solid), Y (dashed).

FIG. 12 depicts cross section of a tube, tube holder plate and support plates; blowup of a section of tube with associated ET signal amplitude (idealized).

DETAILED DESCRIPTION OF THE PREFERRED EMBODIMENT

Eddy Current Basics

Figure 1A:
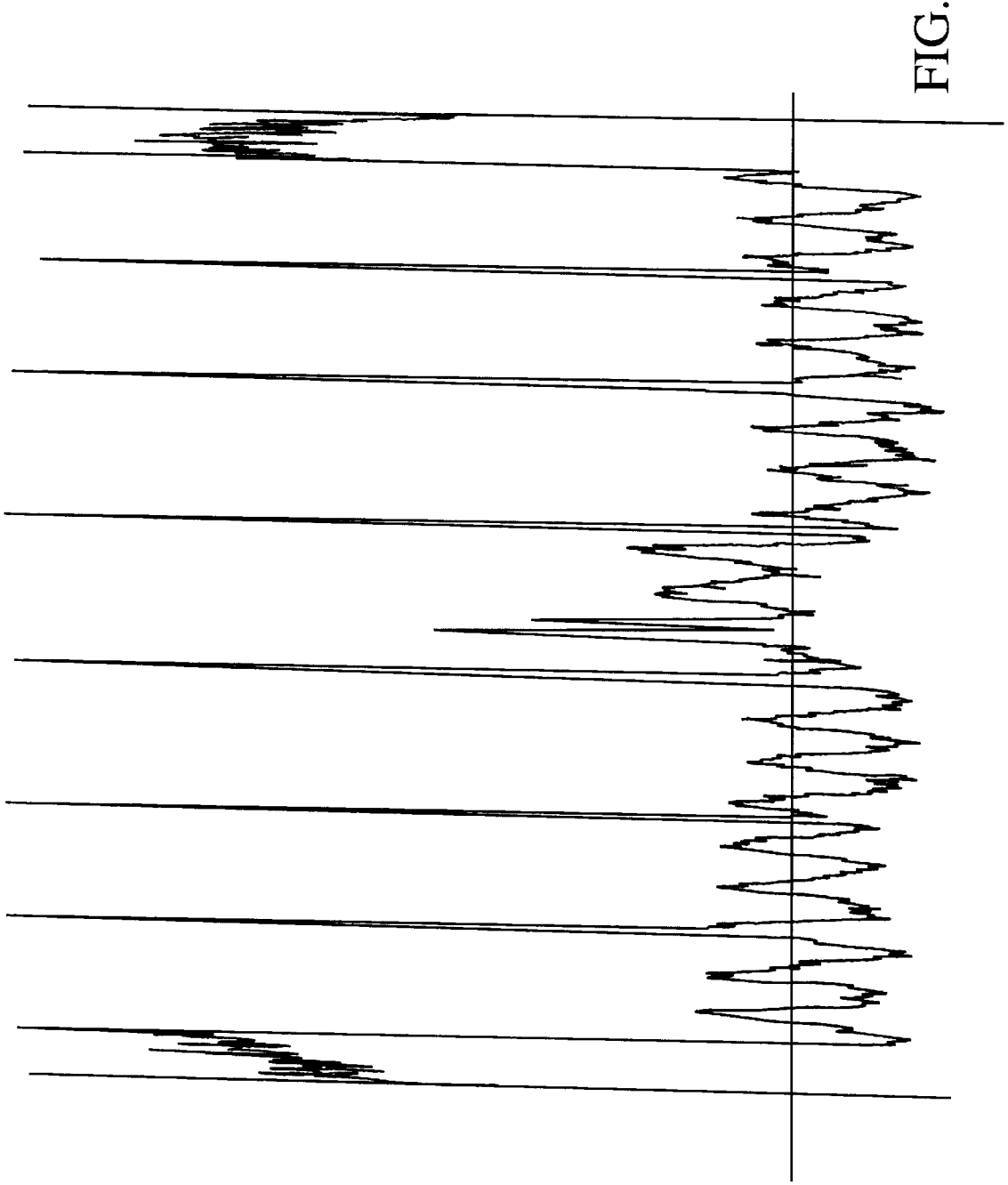
FIG. 1 depicts: (a) an ET signal; (b) a baseline component of signal; and (c) an ET signal with baseline component removed.

The output of eddy current dual bobbin probe measurements is electromagnetic impedance, denoted Z. Impedance Z, comprised of two components, is measured at several locations as the probe is moved over a test piece:

$$Z_k(f) = (R_k(f), Y_k(f)),$$

for P points, k=1,2,3, . . . ,P.
$R_k(f)$ is called the resistive component and $Y_k(f)$ the reactive component of impedance $Z_k(f)$ at point k. The dependence of $Z_k(f)$ on eddy current generation frequency, f, is related to the distance from the probe, within the test piece, that is most sensitive to detection. As f decreases, the distance at which eddy currents are best detected increases. Common practice is to measure the impedance at several frequencies in order to best investigate the entire thickness of the test piece.

At each frequency, eddy current signals are constructed in two ways, i.e., "absolute" and "differential." These designations refer to the manner in which the electrical signals of the eddy current probe are referenced.

Eddy current signals may be represented in two equivalent ways, as time-traces and as Lissajous patterns. In the time-trace view, a data set is represented as two one-dimensional functions of position (equivalently, time), R[M,N]={(k,$R_k$(f)), k=M,M+1, . . . ,N}
Y[M,N]={(k,$Y_k$(f)), k=M,M+1, . . . ,N}, where R[M,N] is resistive impedance from point k=M to point k=N, and Y[M,N] is reactive impedance between the same two points. In the Lissajous pattern view, a data set is represented as one two-dimensional point-ordered line-figure in the impedance plane, Z[M,N]={($R_k$(f),$Y_k$(f)), k=M,M+1, . . . ,N}.

Although both views contain identical information, it is often preferable to use one representation over the other for the sake of convenience of analysis.

Eddy Current Signal Constructs

All automatic signal scanning takes place in the time-trace representation Instead of processing both impedance components individually, however, it is advantageous to construct a one-dimensional signal from the two components, since it is never known in advance which component will display an indication most prominently. In addition, a one-dimensional signal provides a near-halving of the calculational effort required. In this invention, two one-dimensional signals are constructed, as described below.

One-dimensional impedance amplitude, A[M,N], is defined $$A[M,N] = \{\sqrt{[(R_k - R_o)^2 + (Y_k - Y_o)^2]},\ k = M, M+1, \ldots, N\},$$

where ($R_o, Y_o$) are the "null values" of impedance, i.e., the value of Z in featureless regions. Since both components are used to construct amplitude, relevant information is always retained.

$S_{maxmin}$ is another useful one-dimensional signal when the two impedance components are in phase with each other, i.e., $$R_k - \langle R \rangle \approx a(Y_k - \langle Y \rangle),$$

where $\langle R \rangle$ and $\langle Y \rangle$ are averages over the region, and the scalar, a, is a best-fit constant. The minimum and maximum functions are formed at each value of k:

$$I^{min}_k = \min[(R_k(f) - \langle R \rangle), a(Y_k(f) - \langle Y \rangle)]$$

$$I^{max}_k = \max[(R_k(f) - \langle R \rangle), a(Y_k(f) - \langle Y \rangle)]$$

and a resolution-decomposition is performed on both $\{I^{min}\}$ and $\{I^{max}\}$.

The baseline component of $\{I^{max}\}$, $I^{max}$(base), and its peaks-only component, $I^{max}$(peaks)=$0.5(I^{max}_{p/t} + |I^{max}_{p/t}|)$, provides the most prominent contribution to peak shape. Likewise, the baseline component of $\{I^{min}\}$, $I^{min}$(base), and its troughs-only component, $I^{min}$(troughs)=$0.5(I^{min}_{p/t} - |I^{min}_{p/t}|)$, provides the most prominent contribution to trough shape. Thus, $$S_{maxmin} = 0.5[I^{min}(base) + I^{max}(base)] +$$

$$I^{min}(troughs) + I^{max}(peaks)$$

contains the most prominent peak and trough contributions from both impedance components. The reason for the in-phase condition is to prevent a peak in the maximum function from canceling a trough in the minimum function.

Locating and Characterizing an Edge in a Signal Section

Convolve the signal with a Gaussian filter of resolution σ and take its second derivative. The form of the second derivative of an idealized step after it is Gaussian-filtered is $$f_{ab}(s;\sigma) = k\{\exp[-(s-s_a)^2/2\sigma^2] - \exp[-(s-s_b)^2/2\sigma^2]\},$$

where $s_a$ and $s_b$ are the locations of the step, $s_a \leq s_b$, and k is the slope of the step, k=$(f_b - f_a)/(s_b - s_a)$. See FIG. 11.

Figure 11:
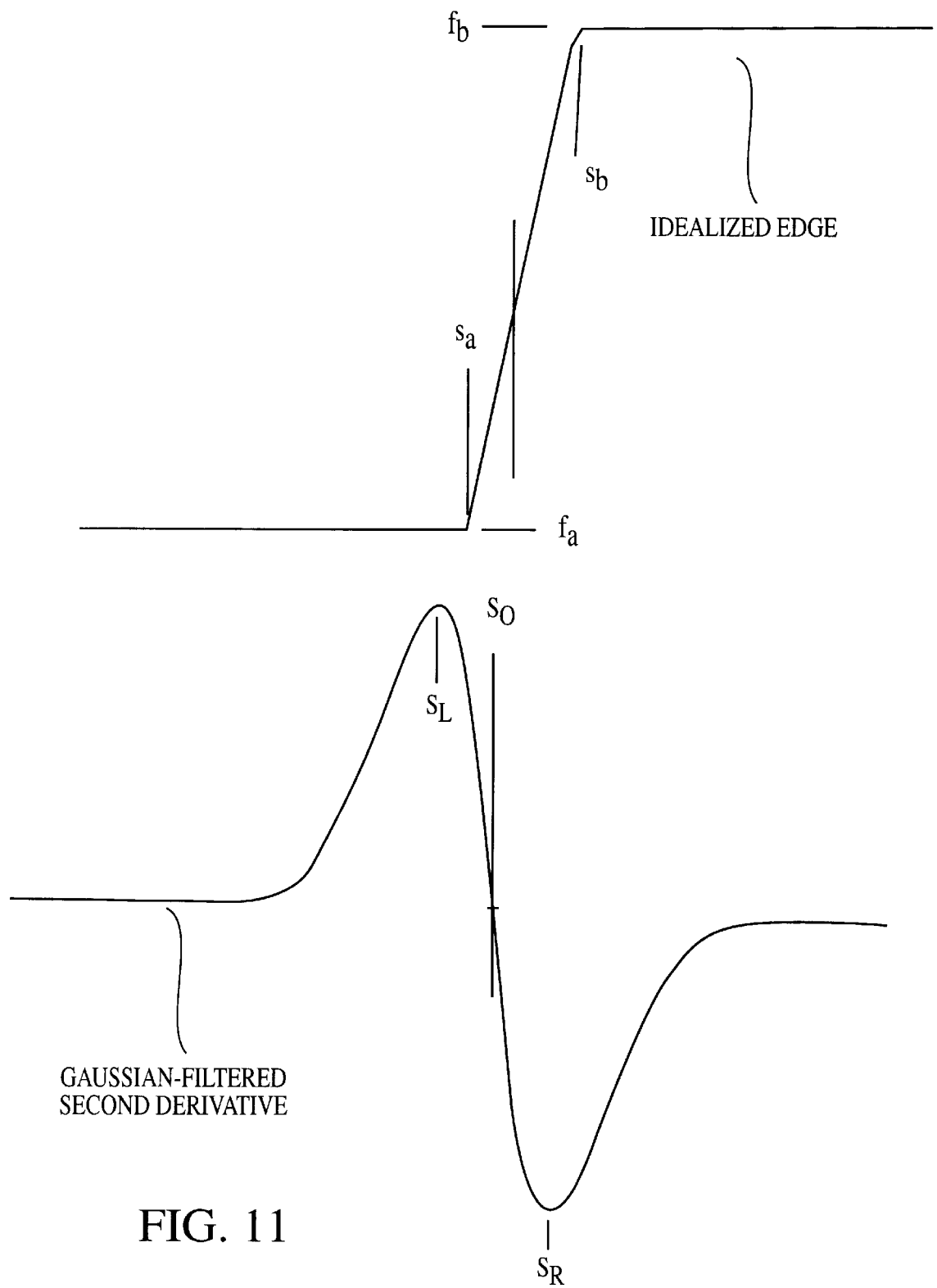
FIG. 11 depicts edge parameters.

Using the Conventions of FIG. 11, $f'_{ab}(s;\sigma) = 0$ at $s = s_L$ and at $s = s_R$.

Therefore $$(s_p - s_a)/(s_p - s_b) = \exp[-[(s_p - s_b)^2 - (s_p - s_a)^2]/2\sigma^2, \quad (B1)$$

where $s_p$ = either $s_L$ or $s_R$.

It is convenient to define $s_e = (s_b + s_a)/2$
delta=$(s_b - s_a)/2$
$D_s = s_p - s_e$
$d_s = D_s/\sigma$
J=delta/σ so that (B1) becomes $$(d_s+J)/(d_s-J)=\exp[2J\,d_s]. \quad (B2)$$

It is best to choose $s_p=s_L$, since, then, $d_s<0$, $J \geq 0$, and the quantity $1/(d_s-J)$ is always defined.

The edge, $s_e$, and the extreme position, $s_L$, are found numerically from the data. J is then computed by numerically solving (B2). A solution can always be found, since the relationship (B2) is satisfied for J=0 (a vertical edge).

From delta and $s_e$, $s_b$ and $s_a$ are obtained. Also at $s=s_e$, $$-\sigma^2 f_{ab}(s_e;\sigma)=2k\text{delta}\,\exp{-(\text{delta}^2/2\sigma^2)},$$

or $$(f_b f_a)=-\sigma^2 f_{ab}(s_e;\sigma)\exp(J^2/2), \quad (B3)$$

which determines the step height. In (B3), the quantity $f_{ab}(s_e;\sigma)$ is computed numerically from the data.

It is this quantity, $(f_b-f_a)$, that is compared to a multiple of the noise level in order to determine whether an edge is sufficiently large.

The present invention is a process that makes use of certain distinguishing features of eddy current technology by applying combinations of tools from a variety of fields, including mathematical morphology and pattern recognition. These tools are used to scan ET signals to identify patterns that indicate the presence of material discontinuities or known structural members in a test piece. In a raw ET signal, some indications may be difficult to detect because the magnitude of their contributions to the signal is comparable to that of the surrounding background. It is the purpose of signal processing to preferentially suppress the background relative to the indication contribution, causing the latter to become visually prominent and, thus, more easily identifiable.

The methods put forward in this invention will be exemplified by a preferred embodiment, processing of eddy current signals taken from inspection of heat exchanger tubing. A sketch of this test system is given in FIG. 12.

Figure 13:
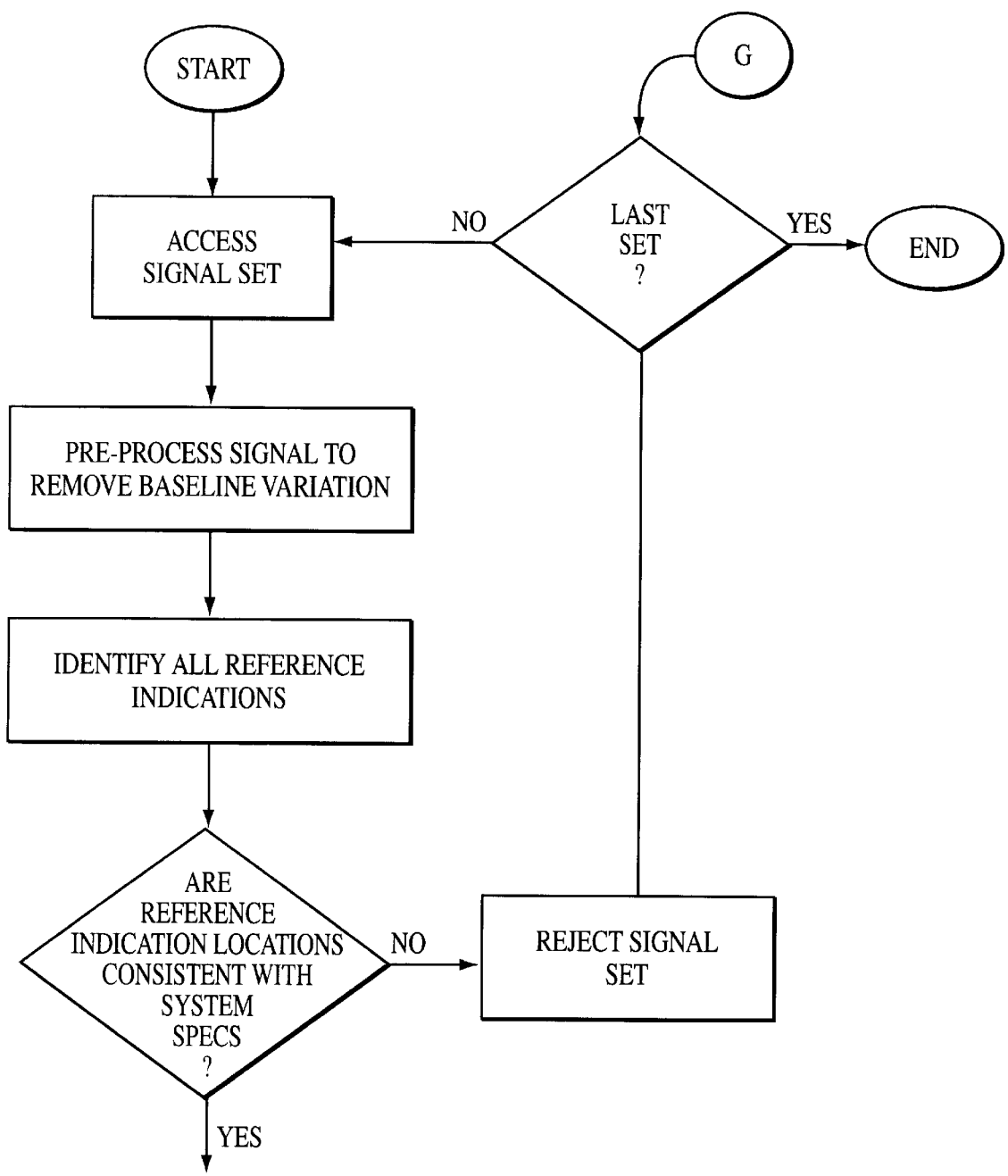
FIGS. 13–13(6) represents the flow charts of salient features of invention.
Figure 13:
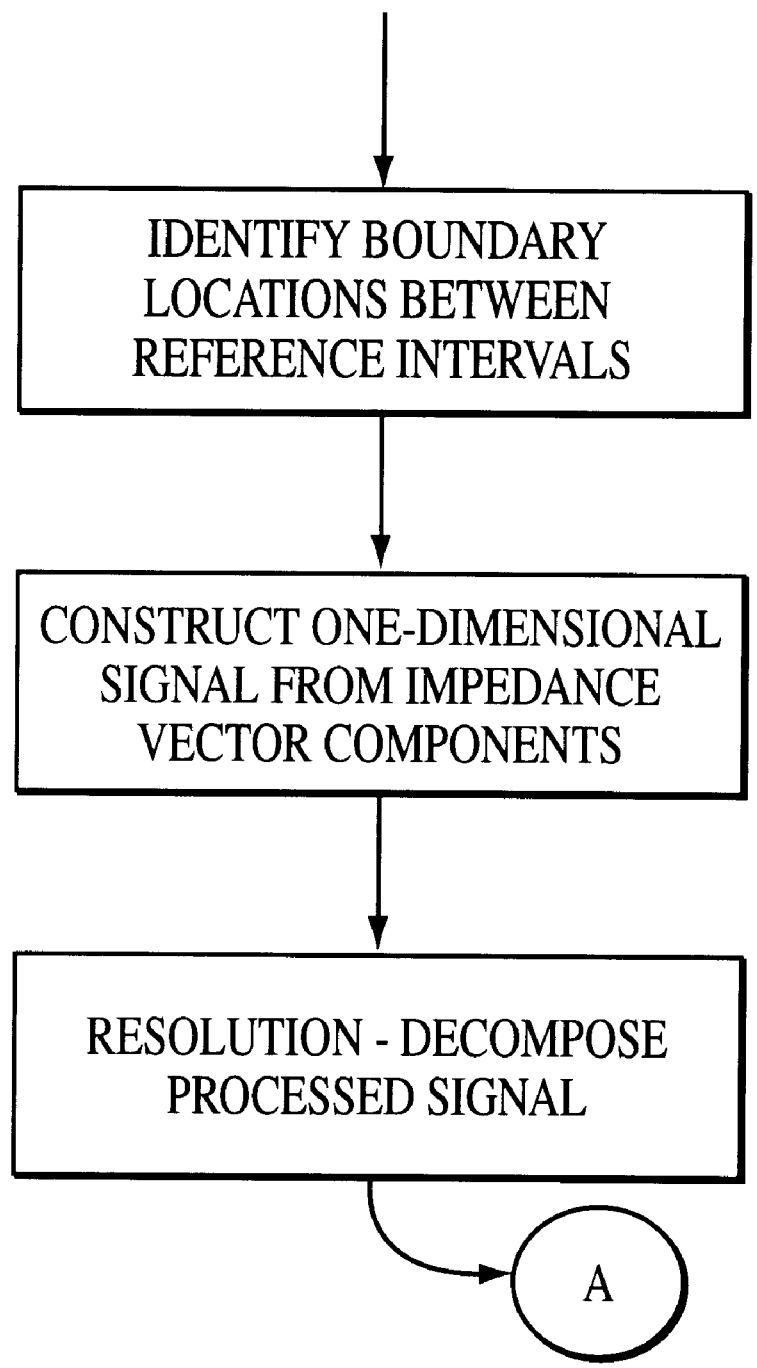
Figure 13:
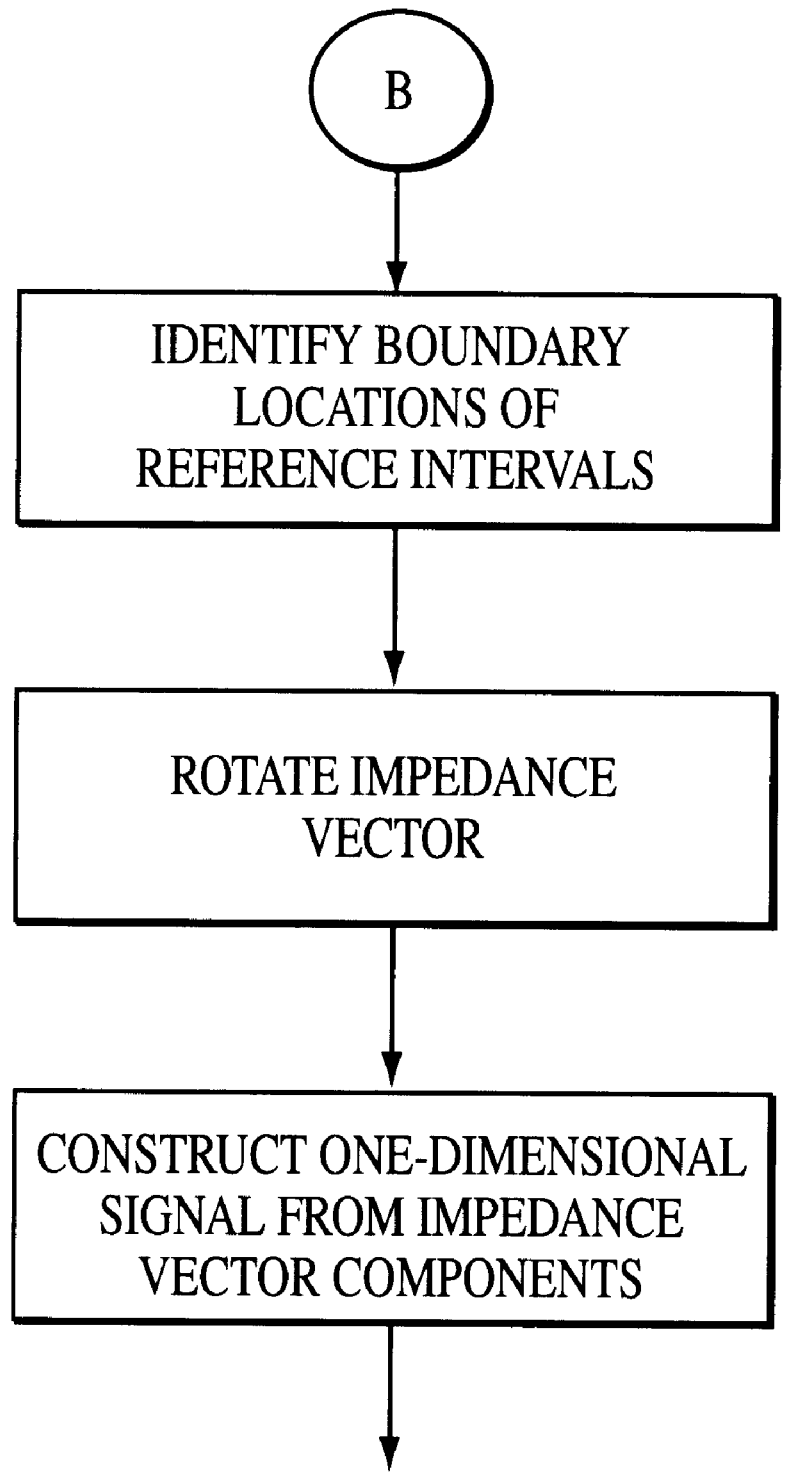
Figure 13:
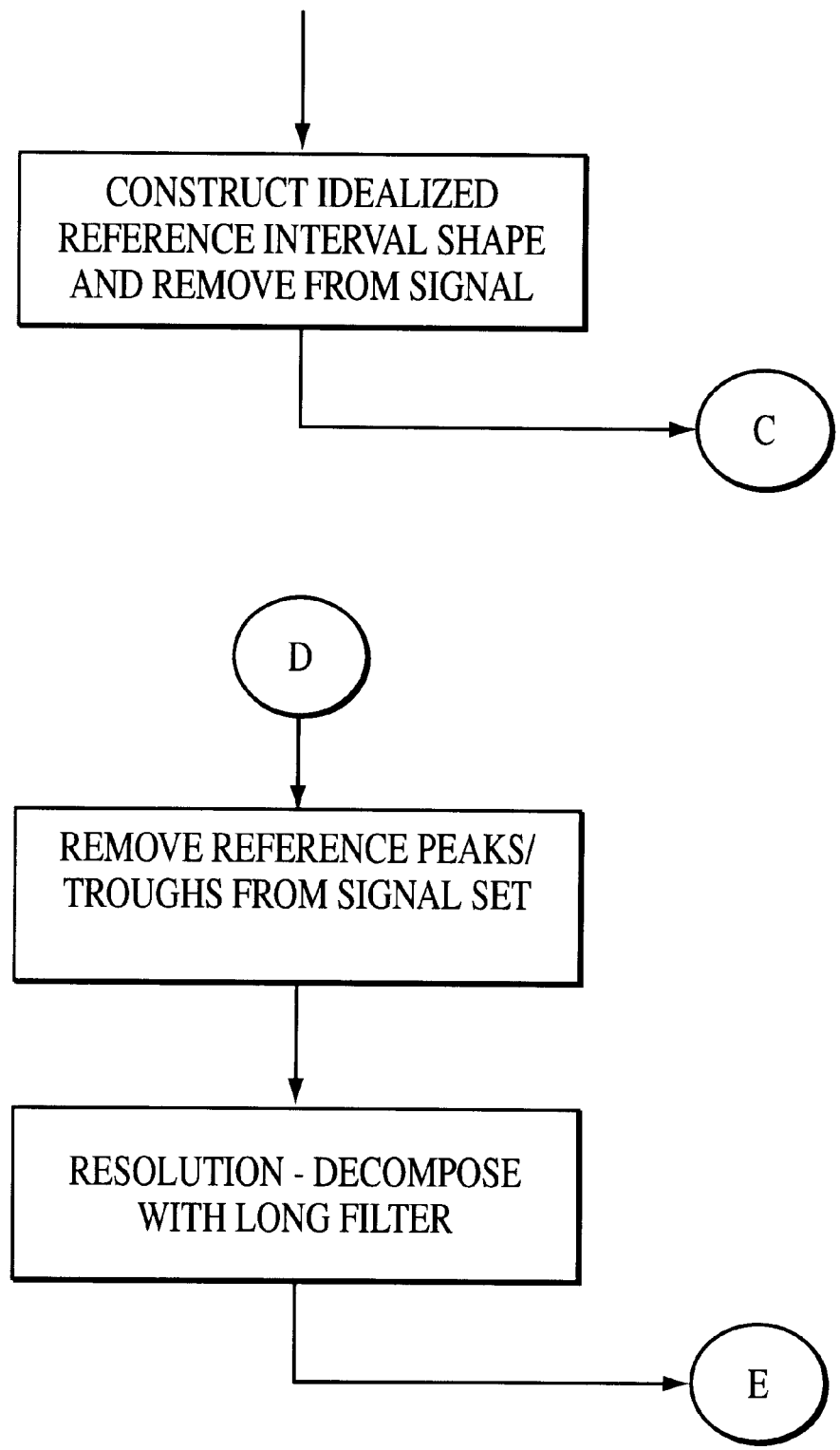
Figure 13:
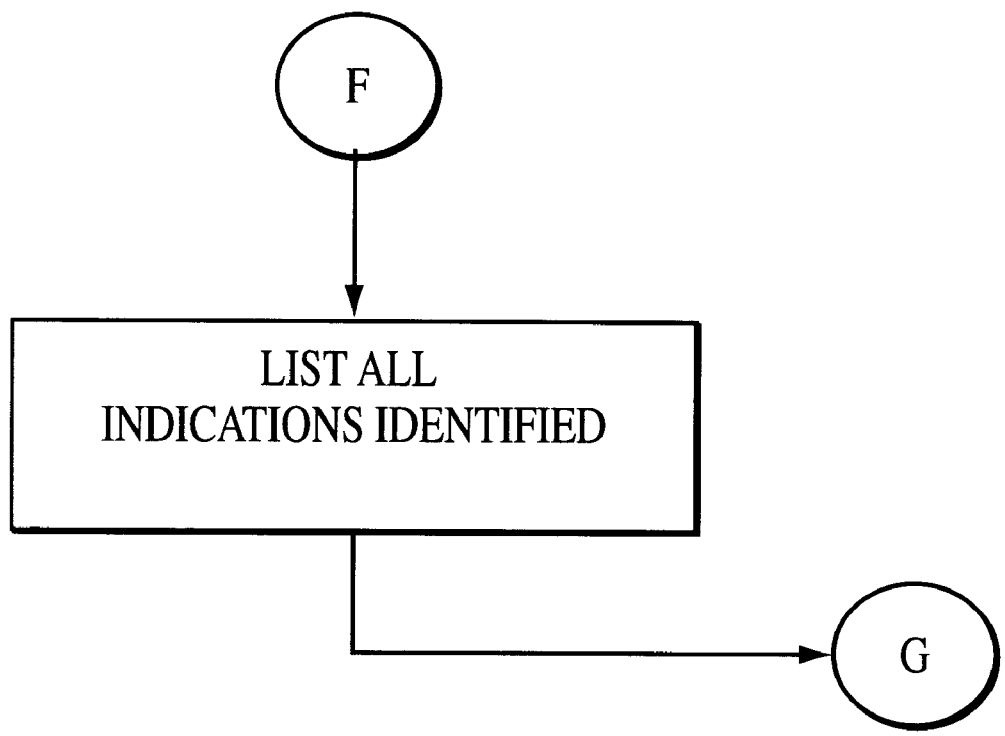
Figure 13:
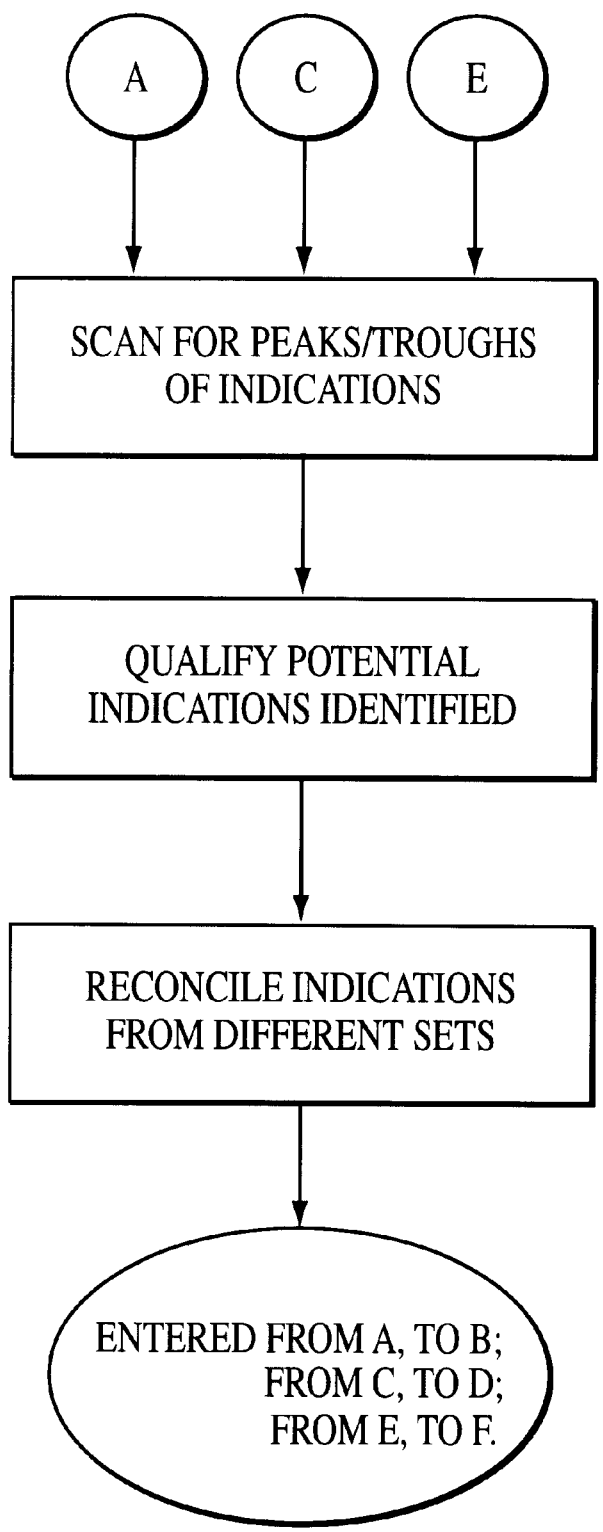

The process steps of the invention are given below, with a flow chart presented in FIG. 13.

A. Pre-processing of ET Signals

Simplifications to the signals are made to facilitate processing. In order to reduce computation time, one signal is constructed out of the two impedance components, {R} and {Y}. Signal patterns not of interest are removed as well.

FIG. 1(a) shows an ET signal that displays narrow peaks (in this case, due to external structural members) on an approximately sinusoidally varying base. Base variation may be caused by probe wobble or by some other cause, but it is unrelated to anomaly indications. Sinusoidal variation is only one of many types of base behavior observed; furthermore, prior to inspection of a signal, no advance information is available to predict what that behavior will be. Base behavior, such as shown in FIG. 1(a), may confound proper detection of anomaly indications by producing large numbers of false indications (tips of the sine baseline posing as anomaly peaks/troughs). Therefore, removal of base variation, with no a priori knowledge of shape, is required before other processing takes place.

Figure 1B:
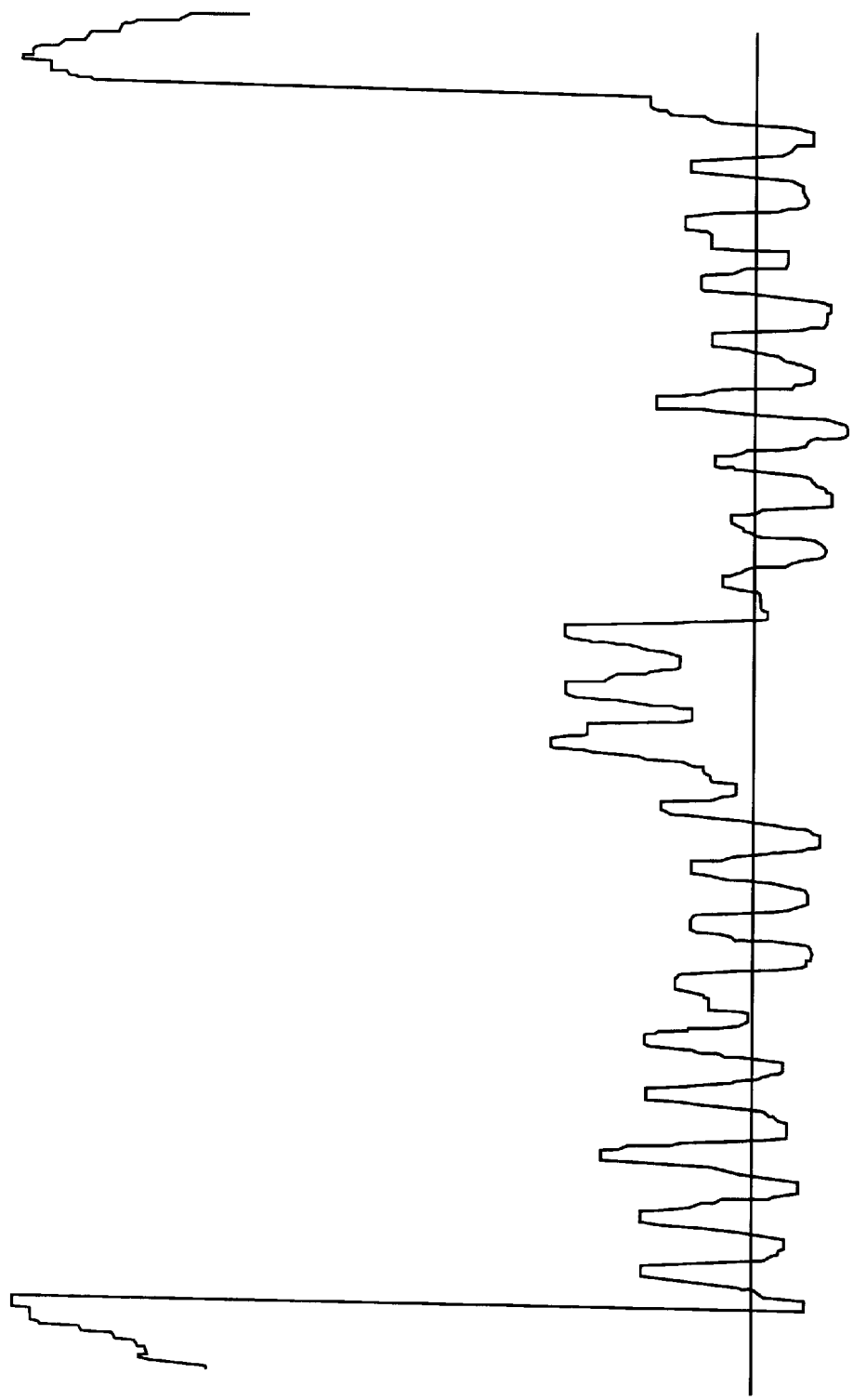
Figure 1C:
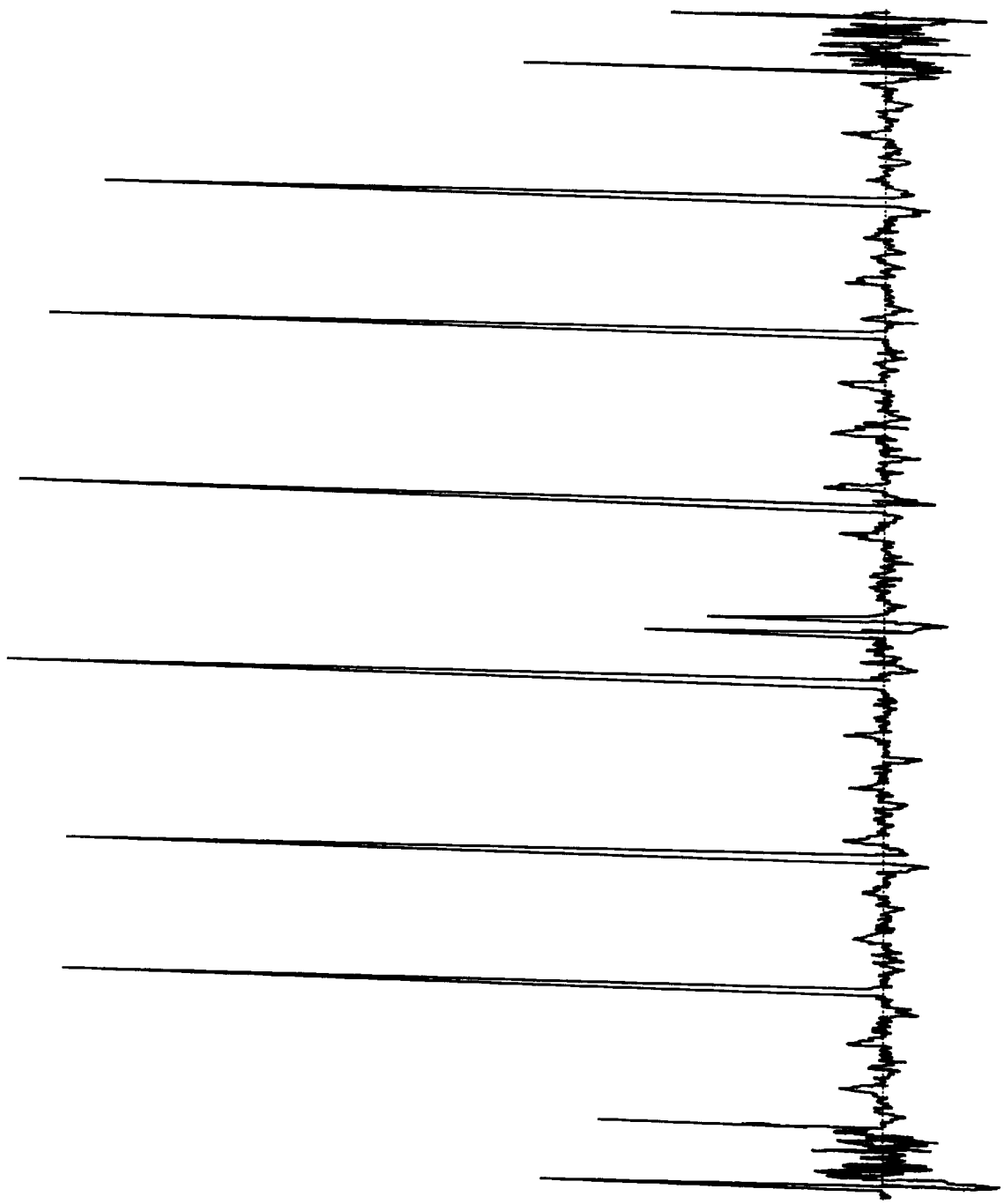

A signal may be decomposed into three independent additive components based on any arbitrarily chosen level of resolution. The component displaying coarse behavior (relative to the chosen resolution level) constitutes the signal's baseline behavior. (The other two components manifest "fine" and "intermediate" behavior, respectively.) Because the components are additive, removal of base variation involves only simple arithmetic subtraction. This simple arithmetic subtraction is illustrated in U.S. patent application No. 08/736,751. The minimum value of resolution chosen corresponds to 1.5 times the thickness of a support structure. FIG. 1(b) shows the baseline component of the signal of FIG. 1(a); FIG. 1(c) is FIG. 1(a) with the baseline component (FIG. 1(b)) removed.

B. Scan for Reference Points

Signal points that correspond to known test piece locations are identified. These points are used to reference other unknown test piece features detected. In the preferred embodiment of this invention, points of reference are external support locations.

For the preferred embodiment of the invention, reference points correspond to all known locations of external tube supports. Near both ends of a heat exchanger tube a sturdy, very thick plate holds the tube in place; the corresponding signal pattern is an edge, denoting a sharp transition in the environment sensed by the probe. See FIG. 12 for an illustration of an edge pattern in a signal. The data set in which the edge is most pronounced is the one selected to scan for these reference points.

Figure 2:
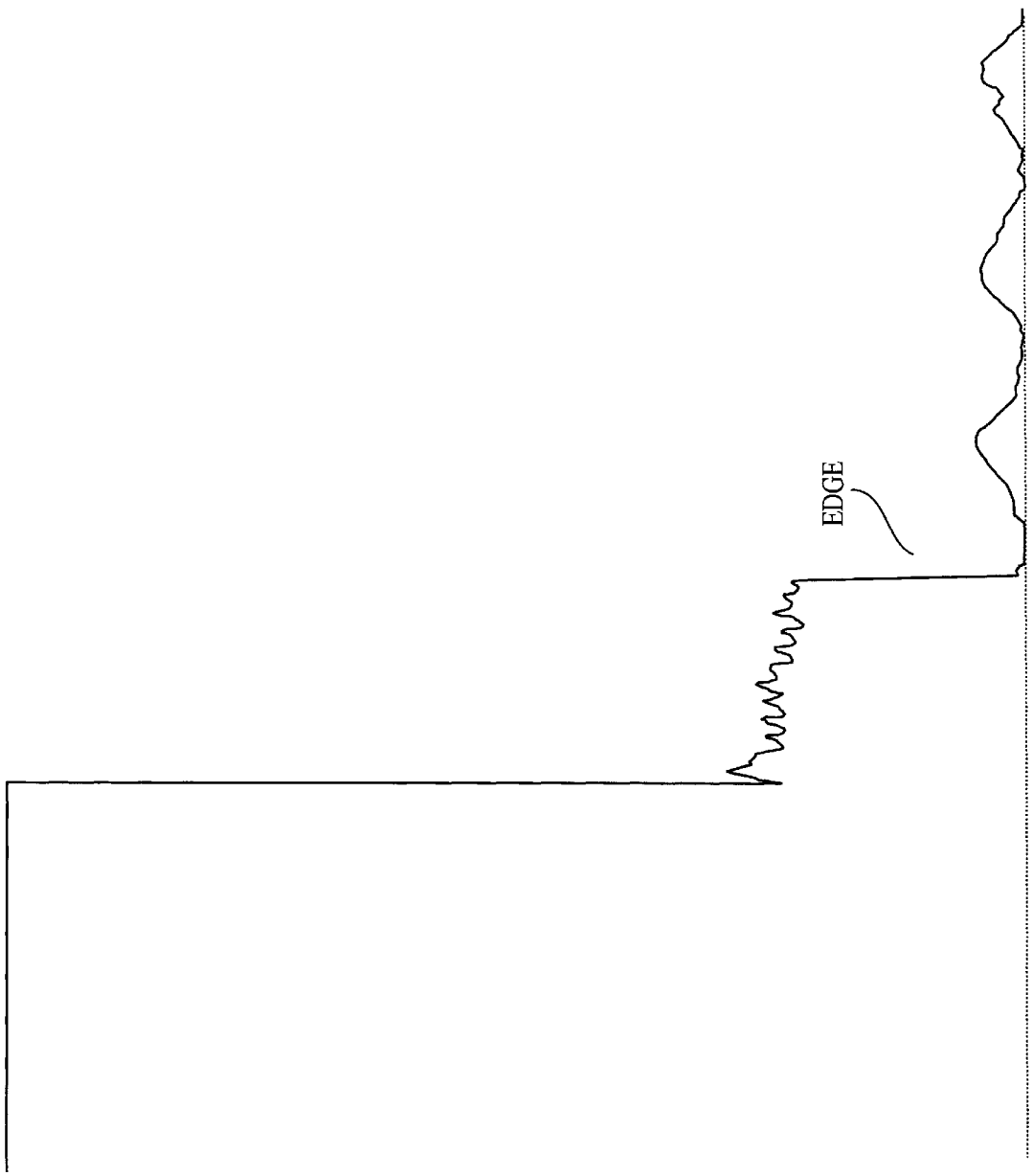
FIG. 2 depicts: an ET signal amplitude near an edge.

Since subsequent signal points are referenced to edges, it is important to establish accurately how many and where an edge is located. Signal appearance near an edge may include many additional patterns, as shown in FIG. 2, which is a typical example of an ET signal amplitude near an edge. Some of the patterns include random noise, another large edge followed by a smooth horizontal line, and a peak due to other test piece features. The following processing sequence results in the suppression of all patterns except the near-end edge.

First, the signal amplitude is constructed from the two impedance components. Signal amplitude contains relevant indication information from both components.

Next, straight sections at the ends of a signal are removed. A straight section is one in which all points lie within a narrow band determined by end values; it represents the probe out of contact with the test piece (before or after insertion).

Figure 3:
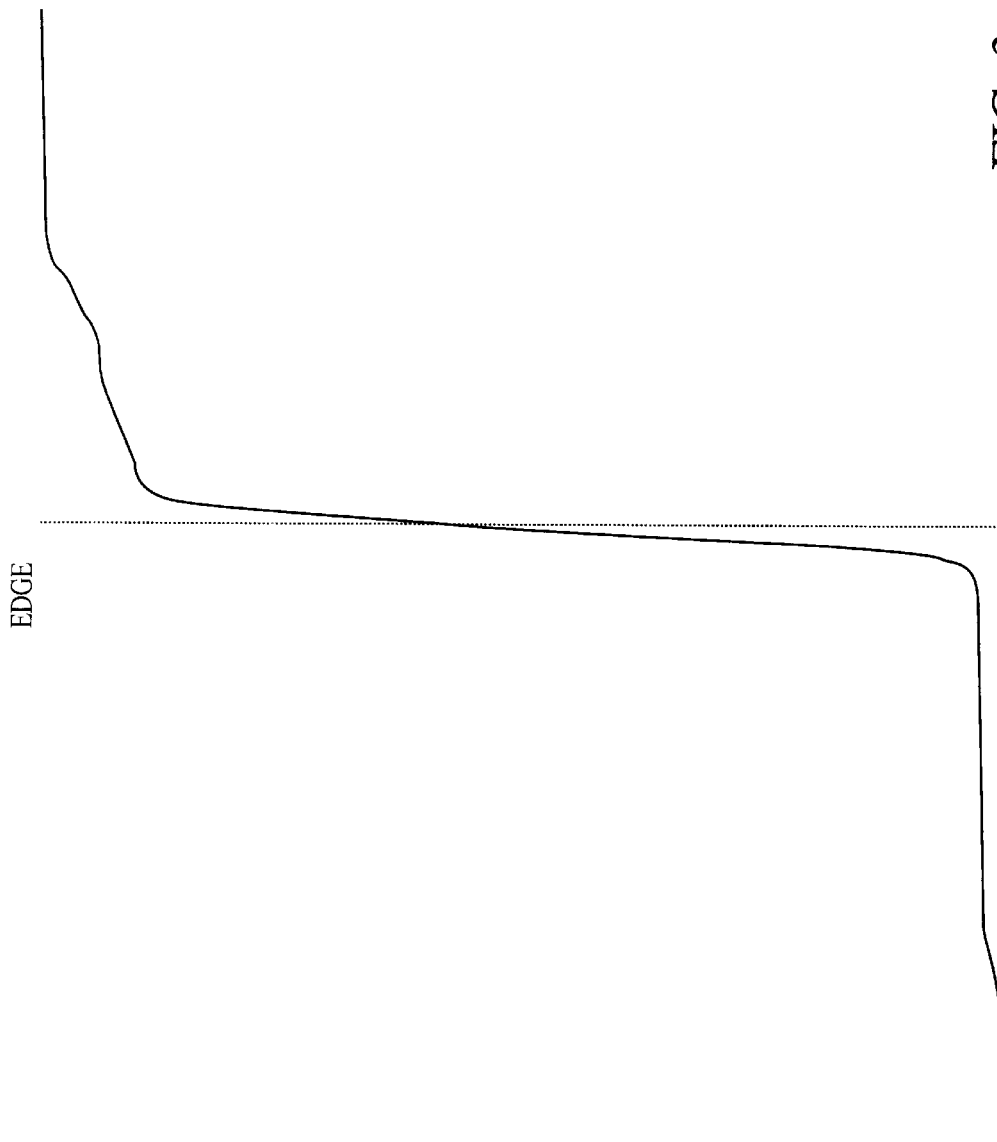
FIG. 3 depicts: a baseline component of FIG. 2 (reversed order), edge identified.

Next, the signal is decomposed into resolution-based components, using a filter of length corresponding to ¾ of the specified holder plate thickness. This value is sufficiently large to exclude from the baseline component other support piece patterns, as well as all random variation, but sufficiently small to include the holder plate pattern. The baseline component of FIG. 2 is shown in FIG. 3 (the ordering of points is inverted to make it similar in appearance to FIG. 11, in which edge parameters are defined).

Next, using a long filter (about 9/10 the number of points in the signal segment), a morphological "tophat", as it is known in the art, is performed. The result of a tophat process is to place the signal in the region corresponding to the test piece (as distinguished from the regions corresponding to the holder plate) near zero value. The edge is then easily identified according to the pattern recognition method described previously. FIG. 3 displays the edge of FIG. 2 obtained with this processing. An edge is verified if its height is three times larger than local noise level (noise level is determined from the fine resolution component in the decomposition described in the preceding step). The value three times noise level was chosen after observation of many ET signals, especially those signals considered very "noisy" by experienced analysts. This is a flexible value, however, that can be changed by any test group. If only one edge is detected in a signal segment, then if the missing edge occurs at the end of a probe's measurement sequence, the signal is rejected because of the possibility of equipment malfunction before completion of the sequence; otherwise, the signal is accepted, considered to represent partial measurement of the test piece. If no edges are detected, then the signal is rejected.

In addition to end supports, other external supports are found along the length of a tube, and these serve as additional points of reference. Furthermore these support locations can be used to qualify a scan. FIG. 12 illustrates external supports along a tube and their associated signal patterns. Using the data set in which the external support patterns are most prominent, the following procedures are performed.

First, the signal amplitude is constructed from the two impedance components. Signal amplitude contains relevant indication information from both components.

Next, for the signal segment between edge locations, baseline variation is removed, similar to baseline removal in the previous section.

Next, a distance that is large relative to the known thickness of the external supports, but less than the smallest of the inter-support spacings, is derived from specified system dimensions. With this distance as filter length for resolution-decomposition, the peaks/troughs component is extracted.

Figure 4:
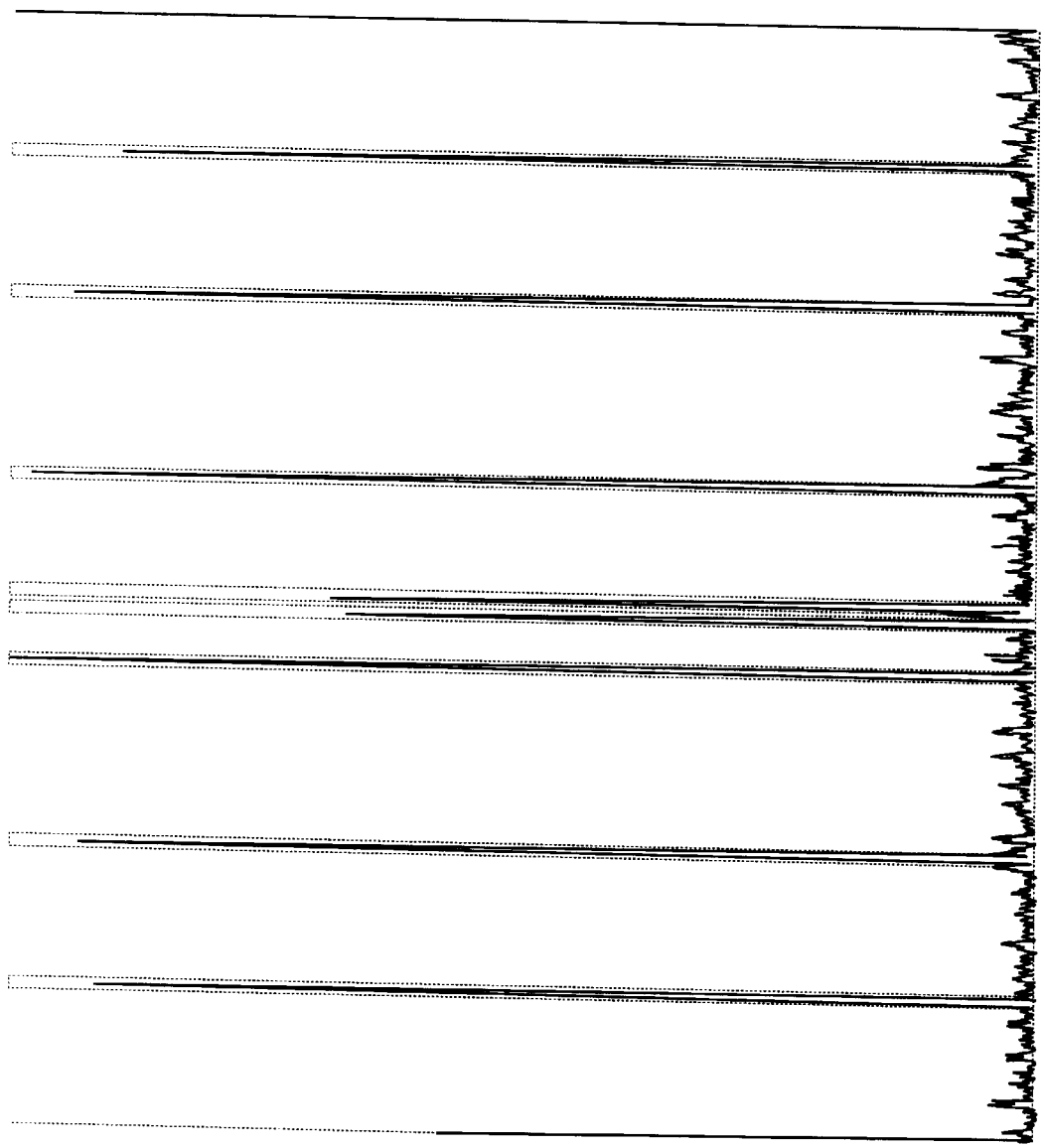
FIG. 4 depicts: a signal amplitude of FIG. 1, support structure peaks (boxed regions) identified.

Next, peaks corresponding to structures wider than the width of the external supports are removed by a morphological tophat operation. Peaks are then identified by an automatic peaks-location method such as disclosed in U.S. Pat. No. 5,737,445; inventors Oppenlander et al., issued Apr. 7, 1998. FIG. 4 shows all relevant peaks of FIG. 1 derived in this manner.

Next, support locations can be verified from support plate design information. From known nominal pull speeds of the ET probe (inch/sec) and measurement rate (points/sec), the corresponding locations of all test piece structures are ascertained. If the test piece was completely scanned, then each identified peak is compared with each specified support location, one for one. If the test piece was not scanned completely, then peak locations are compared for reasonableness, such as computed probe speed (points/inch) between peaks.

The foregoing process reliably identifies signal intervals corresponding to edges and external support structures. A valuable feature of this invention is an automated "flag" indicating possible measurement deficiencies, such as degredation of the ET probe or problems with the electronics or data recording equipment during the test. It is important that such signals are flagged as unanalyzable. Otherwise such suspect data may result in unnecessary repair or limitation in the operation of the heat exchanger.

C. Scan for Point Anomalies

A "point" anomaly, such as a pit, is one whose signal extent is not significantly greater than the signal extent of the probe (in its pull direction). In regions where no competing features are present, indications are identified as peaks or troughs of amplitude significantly greater than local noise amplitude. In regions where other features (such as an external structural member) do appear, additional processing is required to disentangle features.

Prior to scanning, the number and location of discontinuities are not known. Accordingly, there is no one frequency signal that is most appropriate to scan for indications of anomalies. It is, therefore, prudent to process several frequency signals to inspect the entire test piece thickness. In the preferred embodiment, four different signal sets were chosen.

Each signal is divided into two sets of intervals, one set corresponding to support structure locations and the second set corresponding to in-between support structure locations. The latter set of intervals is processed in the following manner.

Figure 5B:
FIG. 5 depicts: a ET signal between two support structure locations: (a) impedance components, R (solid), Y (dashed); (b) $S_{maxmin}$.

The first step is to scan for indications between support structure locations. The one-dimensional signal, $S_{maxmin}$, is constructed from the two-impedance components, $\{R\}$ and $\{Y\}$. This choice is appropriate because, in the absence of any test piece feature, the impedance components are in phase with each other, i.e., $$\{R\} - <R> a(\{Y\} - <Y>),$$

with 'a' being a best-fit scaling factor, and <.> meaning average over all values within an interval. The above relation of the components is well known to those versed in the art of ET inspection. FIG. 5 shows the impedance components, and $S_{maxmin}$ constructed from them, in an interval that includes an anomaly indication.

Coarse resolution behavior, such as overall sinusoidal variation, is removed, in the manner described in section A above.

Figure 6A:
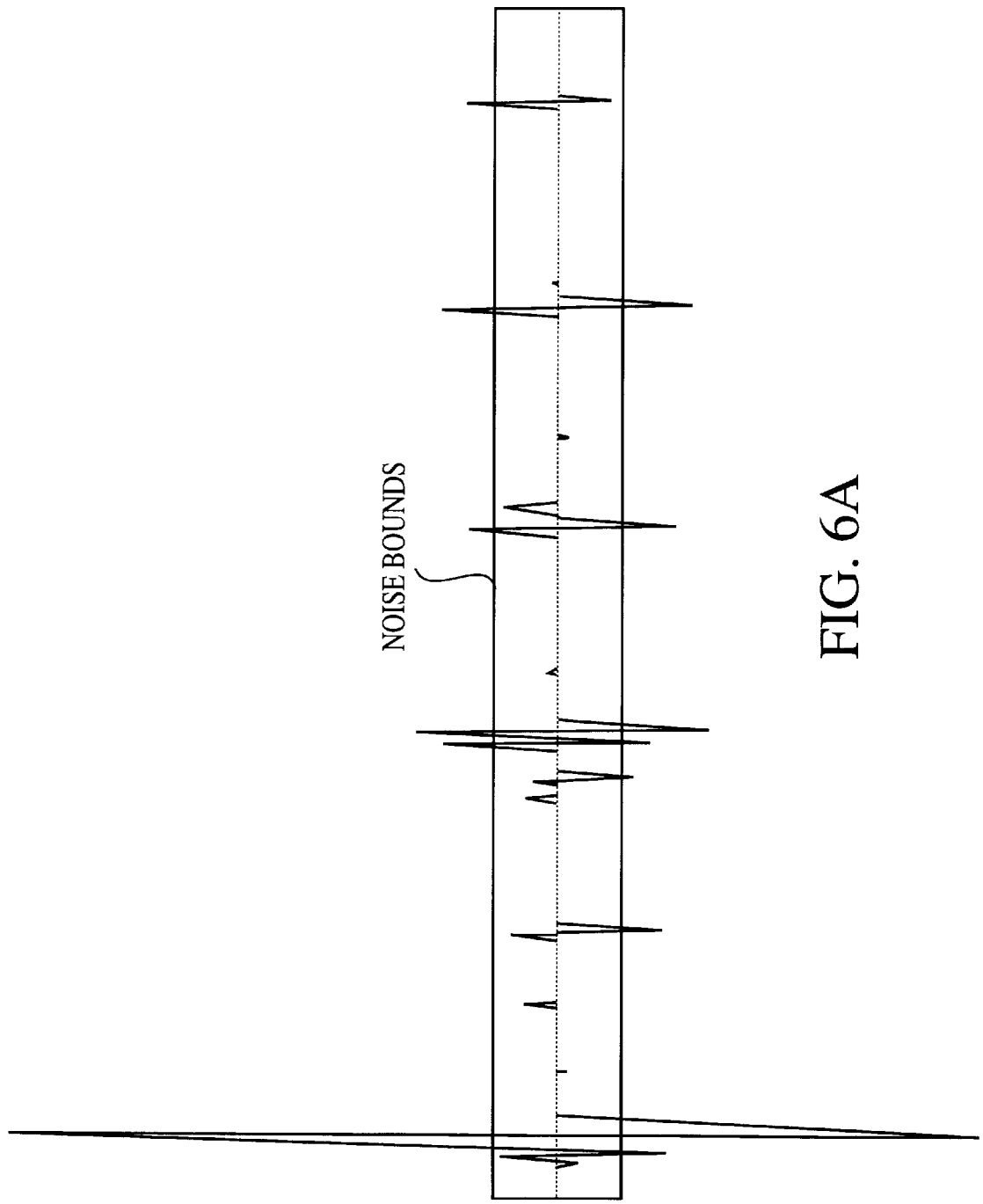
FIG. 6 depicts: peaks/troughs component of FIG. 5(b), (a) with noise bounds; (b) removal of unpaired peaks/troughs.

The processed signal is resolution-decomposed at a level of resolution observed to be typical of point indication patterns. The decomposed peaks/troughs component displays possible indication patterns. The bounding signals used to construct the noise component are used to compute the band of background noise in the interval. FIG. 6(a) displays the peaks/troughs component of FIG. 5(b) together with the locally computed noise band.

Figure 6B:
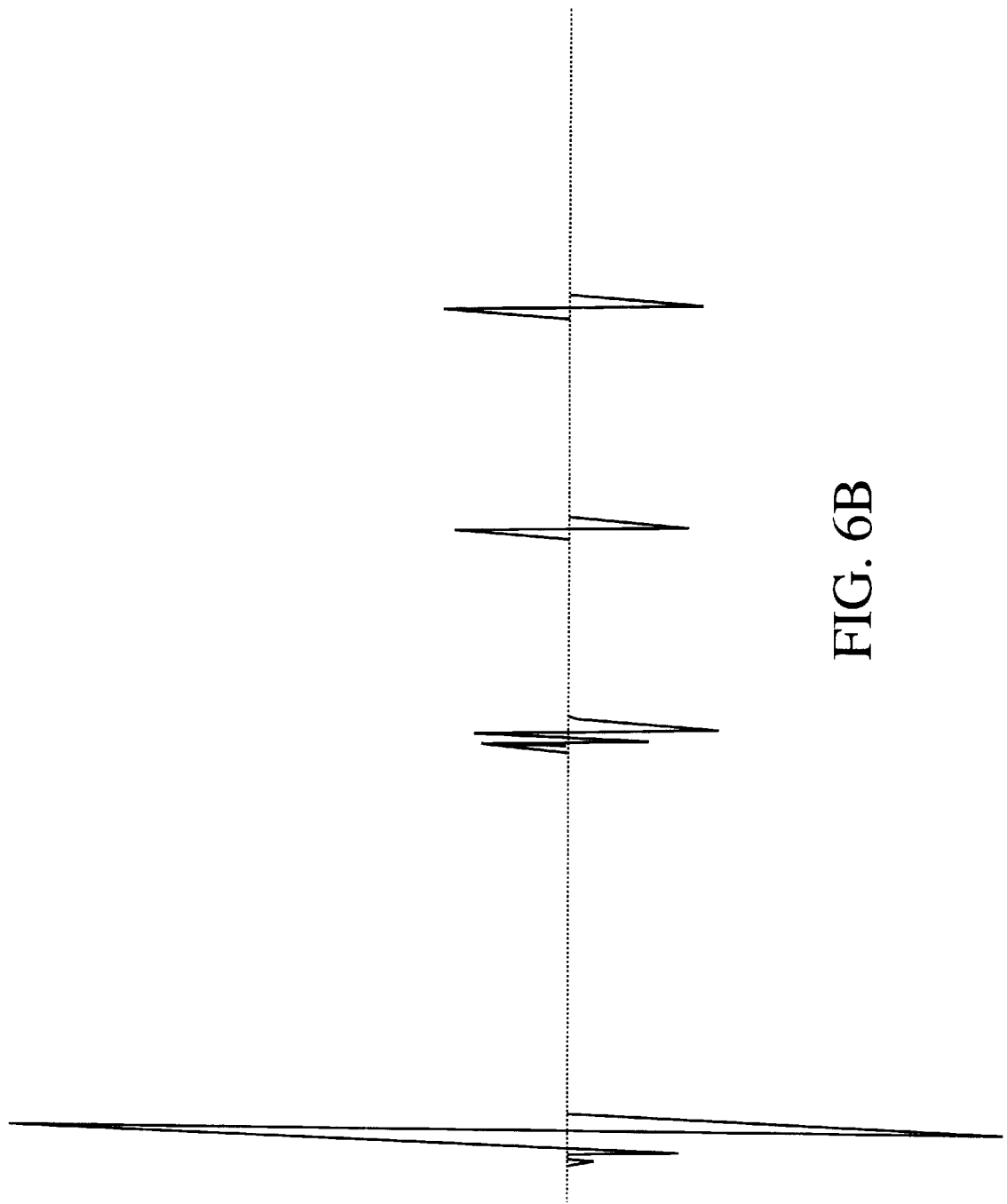

If the signal is of the differential type then only a peak/trough pair in close relative proximity constitutes a valid indication pattern. Any peak without an accompanying trough in a differential signal is disqualified. FIG. 6(b) displays those paired peaks/troughs of FIG. 6(a) that remain after pair qualification.

For a peak/trough pair found in a differential signal, the peak/trough height ("peak-to-peak value", in the art), and for an isolated peak or trough found in an absolute signal, the peak height must exceed the local background level in order to qualify as a reportable indication. The minimum amount that a qualifying signal amplitude must exceed background is an internal test system input parameter that is determined by each test group. In the example shown in FIG. 6, only the leftmost pair qualified as a bona fide indication, when the minimum ratio of signal to noise amplitudes was set equal to 9.

An indication detected in one signal set may represent the same indication detected in another signal set, but with slightly different boundary locations. Indication intervals are compared to determine whether they represent the same test piece feature. If they do, then boundaries are reconciled to produce a final listing of identified indications.

The next step is to scan for indications at support structure locations. Identifying indications within a support structure region is a more difficult task because the signal pattern is an unknown mixture of competing shapes, including patterns of random variation due to equipment noise. When measurement conditions are close to ideal, i.e., no flaws and little random noise, the support structure pattern is known. However, an indication pattern by itself is almost always a shape that is unknown in advance; its existence and location within the support plate interval is also unknown in advance. Furthermore, the exact manner of combination of patterns in a signal is unknown (the assumption of linear superposition of competing signal effects, a fundamental assumption of most signal processing methods, may or may not be true for ET signals; in this invention, it is unnecessary to presume that signals combine linearly, because of the non-linear nature of the signal decomposition methods used). In addition, random noise due to measurement equipment behavior is always present in ET signals.

In order to disentangle the combined pattern to detect and locate an indication shape, the support structure pattern (which, for detection purposes, is considered as background), must be sufficiently suppressed to effectively remove it from view. At the same time, however, the filtering methods must leave enough of the signal intact so that an anomaly indication, if present, may be detected. The method must be sufficiently reliable so that in the event that no significant signal remains after filtering, it may be concluded that no detectable indication exists. The following procedures for detecting anomaly indications satisfy these requirements.

Overall signal baseline behavior is removed to prevent identification of spurious indications. A larger signal interval, that includes but is not restricted to, the support structure interval is used when performing this step.

Figure 7A:
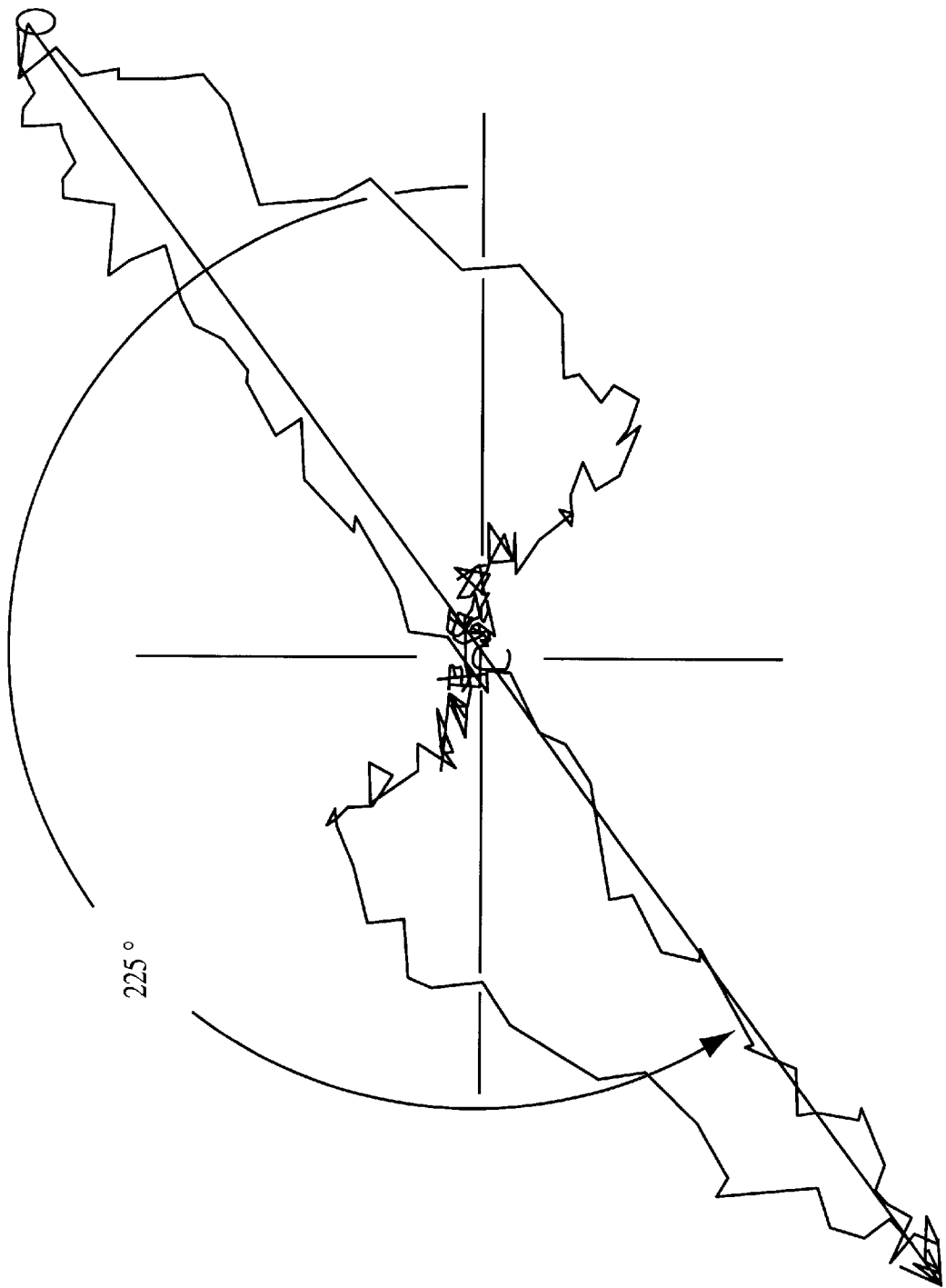
FIG. 7 depicts: a Lissajous patterns rotated to (*a*) 225° (differential); (*b*) 45° (absolute) orientation.
Figure 7B:
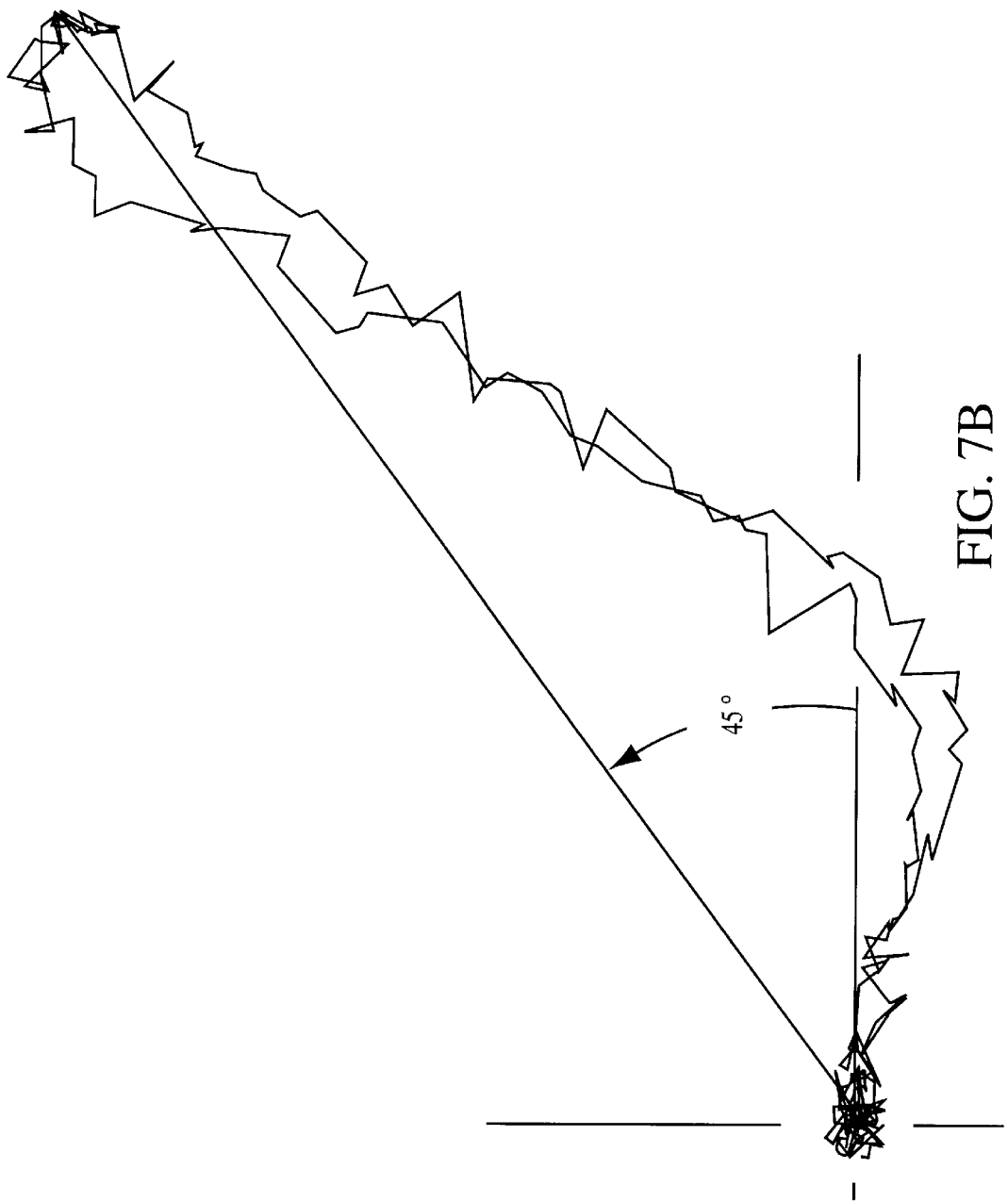

The Lissajous pattern of a support structure in a differential signal resembles a "figure-8" shape; in an absolute signal the same data resembles a curved "figure-V" shape. The Lissajous patterns are rotated so that the differential signals are oriented at 225° and the absolute signals at 45°. FIG. 7 shows Lissajous patterns at these orientations. The purpose of rotation is to orient the known support structure pattern so that $$\{R\}-<R>\approx(\{Y\}-<Y>).$$

After rotation, the support pattern, considered as background for this processing sequence, satisfies the requirements needed for constructing $S_{maxmin}$.

Figure 9A:
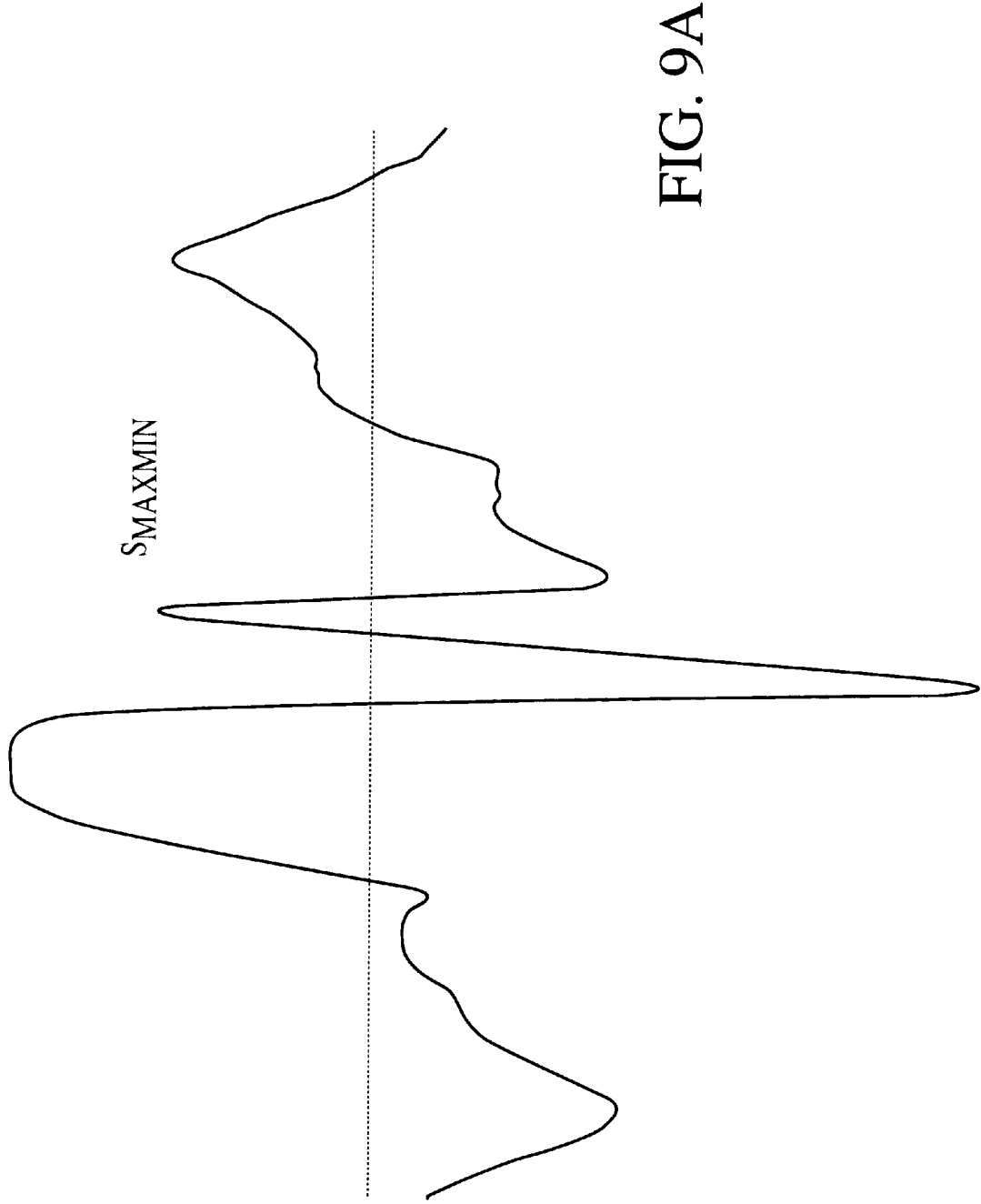
FIG. 9 depicts: (*a*) the $S_{maxmin}$ signal of FIG. 8, smoothed; and (*b*) the idealized support structure pattern.

The two rotated impedance components are combined to construct $S_{maxmin}$. FIG. 8 is an example of two impedance components in a support structure region that contains an indication; FIG. 9(a) is $S_{maxmin}$ constructed from the impedance components of FIG. 8.

Figure 10:
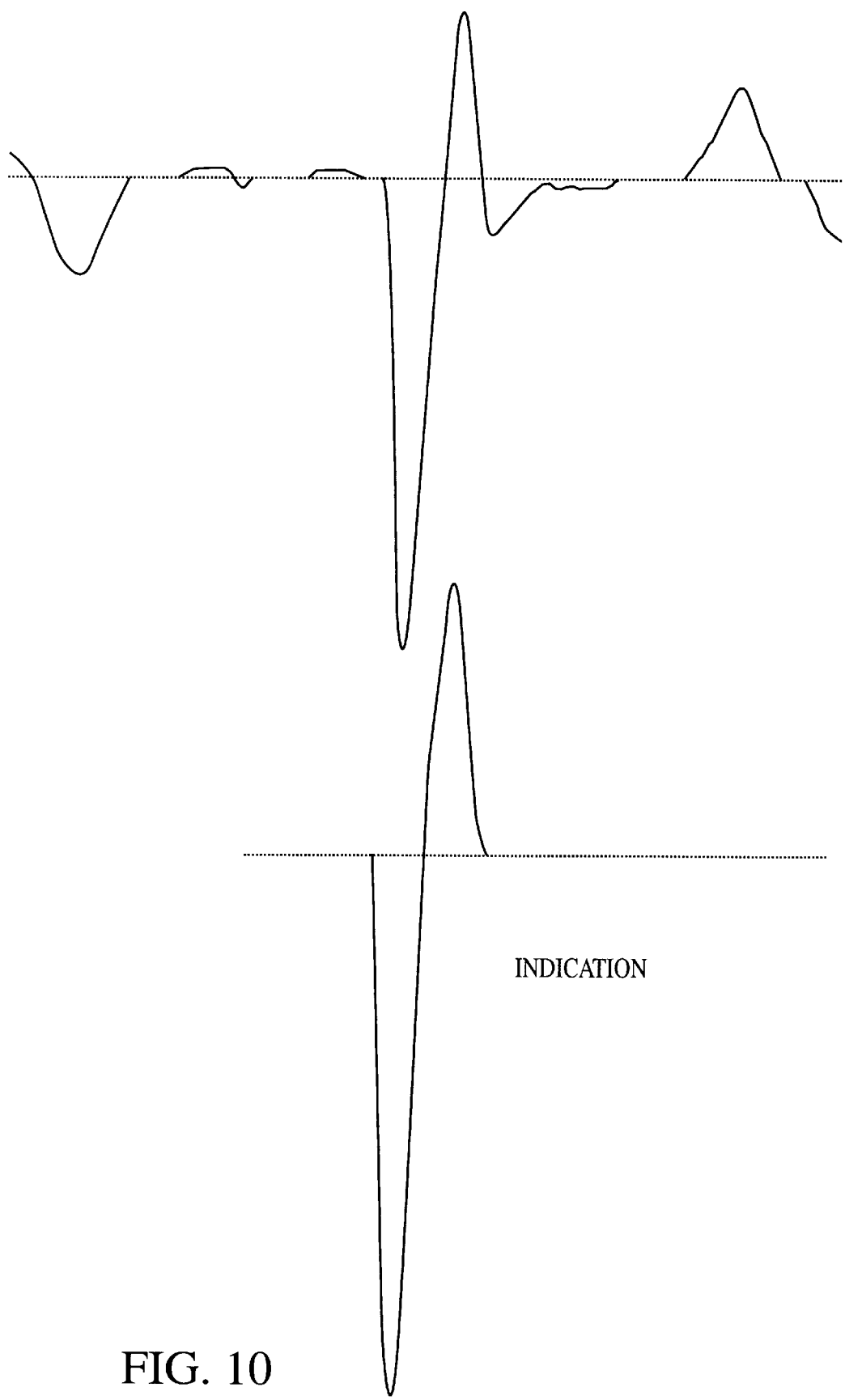
FIG. 10 depicts the support structure pattern after removal of idealized support structure, and after removal of unpaired peaks/troughs.

An idealized support structure pattern is constructed by resolution-decomposing the signal at a resolution level equal to ⅜ the thickness of the support structure. Indications observed in these regions are not greater than this amount and are, therefore, excluded from the baseline component of the decomposition. Subtracting the baseline component from the signal leaves indication patterns, if present, displayed on a zero baseline. FIG. 9(b) is an example of an idealized support pattern constructed from the signal of FIG. 9(a). FIG. 10 displays potential indication patterns that remain after subtraction of FIG. 9(b) from FIG. 9(a), and removal of unpaired peaks/troughs.

Peaks and troughs are now similar in appearance to those that appear in the intervals between supports; the methods of detection are similar to those described in the beginning of this subsection.

Local noise levels are obtained from the between-supports intervals that abut the support structure interval. Indications are qualified as before. Thus, in a differential type signal, only a peak/trough pair of peak-to-peak value that exceeds the required amount compared to background is a qualified indication. Similarly for a peak in an absolute type signal. The one indication that remains in the signal of FIG. 8, after removal of non-pairs, has signal to noise amplitude ratio exceeding the minimum value of 9; the isolated indication pattern is shown in FIG. 10.

If indications are found in different signal sets, they are compared to determine whether they represent the same test piece feature. If so, then boundaries are reconciled to produce a final listing of identified indications.

The methods described above for detecting indications from ET data emulate human visual processes.

D. Scan for Extended Anomalies

Indications of extended anomalies (signal extent significantly greater than the probe's signal extent), are those peaks that remain when all point indications are removed.

In the preferred embodiment of this invention, extended defects are external surface anomalies that appear in signal sets of lowest frequencies. The two lowest frequency sets of absolute type are selected for automated scanning, and each processed in the following manner.

The amplitude signal is constructed from the components, {R} and {Y}.

Amplitude values within intervals corresponding to support locations are replaced by straight lines connecting the signal at the end points of the intervals. Thus no peaks due to support structures remain.

The modified amplitude is resolution-decomposed using a long filter, i.e., of length significantly greater than the associated extent of the probe (in signal points). The noise component provides the background magnitude and the peaks/troughs component provides the wide peaks, should they be present, indicating the presence of extended anomalies.

If indications are found in more than one signal set, they are compared for "sameness", i.e., whether they represent the same test piece feature. If the same, then boundaries are reconciled to produce a final listing of identified indications.

The methods described above for detecting indications of extended anomalies from ET data emulate human visual processes.

While the present invention has been described with respect to an exemplary embodiment thereof, it will be understood by those of ordinary skill in the art that variations and modifications can be effected within the scope and spirit of the invention. The method of the invention is not limited to eddy current signals from heat exchanger tubing inspections, but can be used for any eddy current digital, point-ordered signal.

We claim:

1. A method for automatically and autonomously characterizing the surface of a test material, said test material attached to a support structure, comprising:

(a) generating electromagnetic point-ordered signals as a function of the surface contour of said test material, said point-ordered signals characterized by electromagnetic impedance, said impedance comprising a resistive component and a reactive component;

(b) receiving and enhancing said point-ordered signals by combining said resistive and reactive impedance components into one signal and removing any base variations from the signal;

(c) identifying signal points corresponding to said test material edges by constructing a signal amplitude from the impedance components, removing straight sections at the ends of the signal, decomposing the signal into resolution-based components using a filter, performing a morphological analysis to place the signal in the region corresponding to said test material, and calculating the position of said test material edges;

(d) scanning for point anomalies by dividing the signal into two intervals, the first corresponding to support structure locations and the second corresponding to in-between support structure locations, wherein said second interval is further processed by constructing a one dimensional signal from the impedance components, removing coarse resolution behavior, resolution-decomposing the signal and analyzing the resulting peak/trough indications, and wherein the first interval is further analyzed to remove the support structure signal pattern while preserving detectable anomaly signal;

(e) outputting information about the identity and location of all detected signal features.

2. The method in claim 1 wherein signals are generated at a plurality of frequencies.

3. The method in claim 1 wherein the filter used to decompose the signal in step (c) has a length less than the thickness of the support structure.

4. The method in claim 1 wherein the signal is characterized by signal features and signal noise, and the edge is identified in step (c) in relation to approximately three times the signal noise level.

5. The method in claim 1 wherein the morphological analysis in step (c) is performed using a filter of a length less than the number of points in a signal segment.

6. The method in claim 1 wherein a signal set is rejected for analysis purposes if no test material edges are detected.

7. The method in claim 1 wherein a signal set is rejected for analysis purposes if the number and/or location of the support structure signals are found to be inconsistent with the known design of the support structure.

8. The method in claim 1 wherein the signal in step (d) is resolution-decomposed at a level of resolution typical of point indication patterns.

9. The method in claim 1 wherein there is further scanning for extended surface anomalies.

10. The method in claim 1 wherein before the output of information in step (e), verification is made that the support structures indicated by the signal information are consistent with the known design.

11. The method in claim 1 wherein physical features of said test material are not known in advance.

* * * * *